United States Patent
Zhao et al.

(10) Patent No.: US 12,099,027 B2
(45) Date of Patent: Sep. 24, 2024

(54) SYSTEMS AND METHODS FOR WATER DETECTION

(71) Applicant: Apple Inc., Cupertino, CA (US)

(72) Inventors: Ge Zhao, San Francisco, CA (US); Terrance P. Kao, Saratoga, CA (US); Muhammad Ahmadi, Santa Clara, CA (US); Bin Fan, Sunnyvale, CA (US)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 18/348,950

(22) Filed: Jul. 7, 2023

(65) Prior Publication Data

US 2024/0011926 A1 Jan. 11, 2024

Related U.S. Application Data

(60) Provisional application No. 63/368,035, filed on Jul. 8, 2022.

(51) Int. Cl.
| | | |
|---|---|---|
| *G06F 3/044* | (2006.01) | |
| *A61B 5/00* | (2006.01) | |
| *A61B 5/11* | (2006.01) | |
| *G01N 27/02* | (2006.01) | |
| *G06F 3/041* | (2006.01) | |

(52) U.S. Cl.
CPC ............ *G01N 27/02* (2013.01); *A61B 5/1118* (2013.01); *A61B 5/681* (2013.01); *A61B 5/6844* (2013.01); *G06F 3/0416* (2013.01); *G06F 3/0414* (2013.01); *G06F 3/044* (2013.01)

(58) Field of Classification Search
None
See application file for complete search history.

(56) References Cited

U.S. PATENT DOCUMENTS

| | | | | |
|---|---|---|---|---|
| 6,580,943 B2* | 6/2003 | Nissila | .................. | A61B 5/282 |
| | | | | 600/509 |
| 8,982,097 B1* | 3/2015 | Kuzo | .................. | G06F 3/04186 |
| | | | | 345/174 |
| 11,487,377 B2* | 11/2022 | Park | ...................... | G06F 3/0482 |
| 2012/0062508 A1* | 3/2012 | Liu | ........................ | G06F 3/0447 |
| | | | | 345/174 |
| 2014/0235180 A1* | 8/2014 | Fortin | ................. | G06F 3/03543 |
| | | | | 455/67.16 |
| 2015/0009173 A1* | 1/2015 | Rodzevski | ............ | G06F 3/0418 |
| | | | | 345/174 |
| 2015/0022481 A1* | 1/2015 | Andersson | .......... | G06F 3/04186 |
| | | | | 345/174 |

(Continued)

FOREIGN PATENT DOCUMENTS

GB 2502982 A 12/2013

OTHER PUBLICATIONS

Heikenfeld et al., "Wearable Sensors: Modalities, Challenges, and Prospects", Lab on a Chip, vol. 18, No. 2, Nov. 28, 2017, pp. 217-248.

*Primary Examiner* — Sepehr Azari
(74) *Attorney, Agent, or Firm* — Kubota & Basol LLP

(57) ABSTRACT

An electronic device can detect whether the device is submerged in water using measurements from one or more electrodes. In some examples, the water detection can differentiate between a user contact with an electrode or the electrode submerged in water. In some examples, the detection of water can trigger water-related functions on device.

20 Claims, 11 Drawing Sheets

(56) References Cited

U.S. PATENT DOCUMENTS

| | | | |
|---|---|---|---|
| 2015/0277720 A1* | 10/2015 | Thorson | G06F 3/0482 345/174 |
| 2016/0148034 A1* | 5/2016 | Kremin | G06V 40/1306 382/124 |
| 2016/0173089 A1* | 6/2016 | Kao | H03K 17/962 200/600 |
| 2016/0179243 A1* | 6/2016 | Schwartz | G06F 3/0446 345/174 |
| 2019/0064998 A1* | 2/2019 | Chowdhury | G03B 17/08 |
| 2019/0129556 A1* | 5/2019 | Hwang | G06F 3/04166 |
| 2020/0104021 A1* | 4/2020 | Bylenok | G06F 3/02 |
| 2020/0363891 A1* | 11/2020 | Yancey | G01R 27/2605 |
| 2021/0258014 A1* | 8/2021 | Tang | H03M 1/60 |
| 2023/0401886 A1* | 12/2023 | Dhindhsa | G06F 3/0414 |

\* cited by examiner

SYSTEMS AND METHODS FOR WATER DETECTION

CROSS-REFERENCE TO RELATED APPLICATIONS

This application claims priority to U.S. Provisional Application No. 63/368,035 filed Jul. 8, 2022, entitled "SYSTEMS AND METHODS FOR WATER DETECTION," the entire disclosure of which is hereby incorporated by reference for all proper purposes.

FIELD

This relates generally to systems and methods for water detection, and more particularly, to detecting whether a wearable device is in contact with a wearer's skin, submerged in water, or none of the above using measurements from one or more electrodes on the wearable device.

BACKGROUND

Electronic devices include various sensors. The performance of some of the various sensors may be dependent on the contact conditions. Accordingly, there is a need for systems and methods to determine contact conditions.

SUMMARY

This relates to systems and methods for water detection. In some examples, the water detection can include detecting whether a device (e.g., wearable device, a mobile device, etc.) is submerged in water using measurements from one or more electrodes on the device. In some examples, the water detection can differentiate between a user contact with an electrode or the electrode submerged in water. In some examples, the detection of water or user contact can be used for device operation. For example, the detection of water can trigger water-related functions on device. The device can comprise one or more measurement electrodes, one or more reference electrodes, and processing circuitry coupled to the electrodes. In some examples, the processing circuitry can include a stimulation circuit. The stimulation circuit can drive a stimulation signal on one of the electrodes. In some examples, the processing circuitry can detect a signal resulting from the stimulation signal and based on the detected signal, determine whether the wearable device is in contact with the user's skin, submerged in water, or none of the above.

In some examples, upon determining that the device is submerged, the processing circuitry triggers one or more water-related modes of the device. In some examples, upon determining that the device is contacting the user's skin, the processing circuitry triggers one or more measurement related modes of the device.

DETAILED DESCRIPTION

In the following description of examples, reference is made to the accompanying drawings which form a part hereof, and in which it is shown by way of illustration specific examples that can be practiced. It is to be understood that other examples can be used and structural changes can be made without departing from the scope of the disclosed examples.

This relates to systems and methods for water detection. In some examples, the water detection can include detecting whether a device (e.g., wearable device, a mobile device, etc.) is submerged in water using measurements from one or more electrodes on the device. In some examples, the water detection can differentiate between a user contact with an electrode or the electrode submerged in water. In some examples, the detection of water or user contact can be used for device operation. For example, the detection of water can trigger water-related functions on device. The device can comprise one or more measurement electrodes, one or more reference electrodes, and processing circuitry coupled to the electrodes. In some examples, the processing circuitry can include a stimulation circuit. The stimulation circuit can drive a stimulation signal on one of the electrodes. In some examples, the processing circuitry can detect a signal resulting from the stimulation signal and based on the detected signal, determine whether the wearable device is in contact with the user's skin, submerged in water, or none of the above.

In some examples, upon determining that the device is submerged, the processing circuitry triggers one or more water-related modes of the device. In some examples, upon determining that the device is contacting the user's skin, the processing circuitry triggers one or more measurement related modes of the device.

Figure 1A:
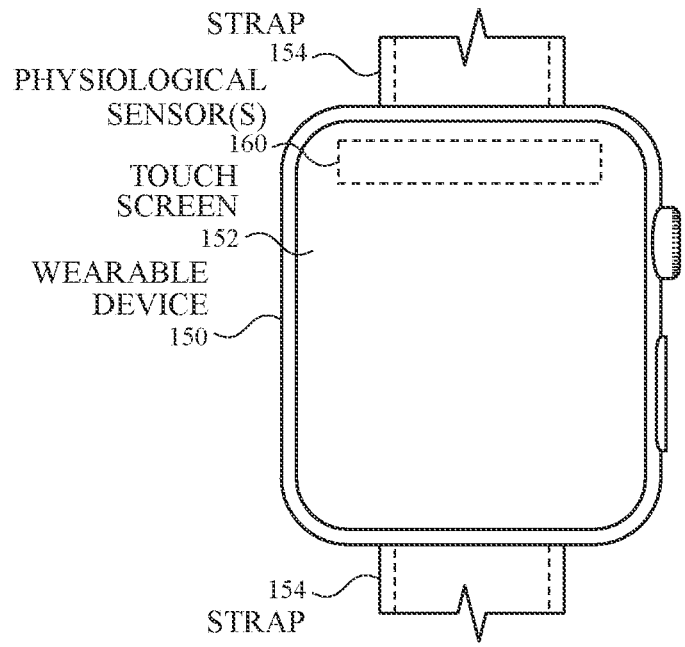
FIGS. 1A-1B illustrate example systems including one or more electrodes according to examples of the disclosure may be implemented.
Figure 1B:
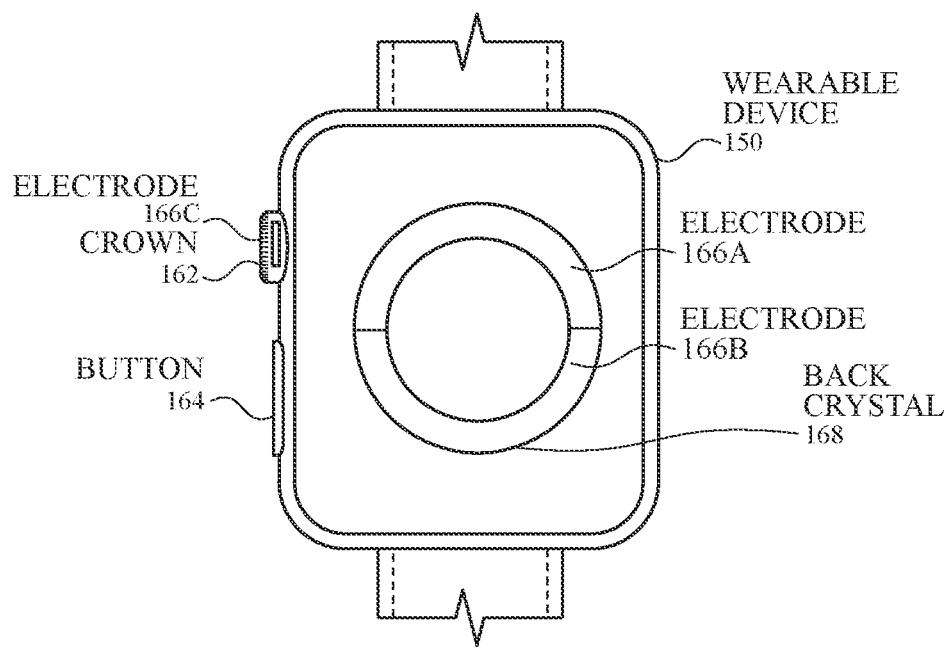

FIGS. 1A-1B illustrate example systems including one or more electrodes and in which contact and/or submerge detection according to examples of the disclosure may be implemented. FIG. 1A illustrates an example wearable device 150 (e.g., a watch) that includes a strap 154, a touch screen 152, and physiological sensor(s) 160 (e.g., an ECG sensing system including one or more measurement electrodes, one or more reference electrodes, and processing circuitry coupled to the electrodes). FIG. 1B illustrates an example view of the back side of wearable device 150 that includes electrodes 166A-C of physiological sensor 160. Physiological sensor 160 can include electrode 166C implemented in crown 162 of wearable device 150, an electrode implemented in button 164 of wearable device 150. As part of the back side of the wearable device 150, there is a back crystal 168 that contacts the user's skin and includes electrode 166A and/or electrode 166B. Additionally or alternatively, the physiological sensor 160 can include a measurement electrode (e.g., electrode 166C in crown 162), a first reference electrode (e.g., electrode 166A on the backside of the back crystal 168 of wearable device 150) and a second, ground reference electrode (electrode 166B on the back crystal 168 of wearable device 150). In some examples, the physiological sensor 160 can include a measurement electrode in button 164 in addition to or instead of measurement electrode 166C in crown 162. In some examples, the physiological sensor 160 can include more than one measurement electrode and more than two reference electrodes. Although described as including a physiological sensor 160, in some examples, the wearable device may not include a physiological sensor 160, but may still include electrodes (e.g., external electrodes) for detection of submersion in water. It is understood that the above physiological sensor(s) can be implemented in other wearable and non-wearable devices, including dedicated devices for the acquisition and/or processing of physiological signals (e.g., ECG (electrocardiogram) signals). It is understood that water detection described herein can be implemented in other wearable and non-wearable devices. It is understood that although wearable device 150 includes a touch screen 152, the display of a notification for initiating one or more water-related modes described herein can be performed on a touch-sensitive or non-touch-sensitive display of the device, of a separate device or a standalone display. Additionally it is understood that although the disclosure herein primarily focuses on determining whether the wearable device is contact with the user's skin, submerged in water, and/or none of the above, the disclosure can also be applicable to determining other states, such as, whether the wearable device is in the shower, rain, as opposed to being submerged in liquid.

In some examples, the electrodes of physiological sensors 160 can be dry electrodes which can be measurement electrodes configured to contact a skin surface and capable of obtaining an accurate signal without the use of a conducting or electrolytic gel. In some variations, one or more reference electrodes may be located on a wrist-worn device, such as a bracelet, wrist band, or watch, such that the reference electrodes can contact the skin in the wrist region, while one or more measurement electrodes can be configured to contact a second, different skin region (e.g., a finger of a hand opposite the wrist wearing the wrist-worn device). In some examples, the measurement electrode(s) can be located on a separate component from the reference electrode(s). In some examples, some or all of the measurement electrode(s) can be located on a wrist or finger cuff, a fingertip cover, a second wrist-worn device, a region of the wrist-worn device that can be different from the location of the reference electrode(s), and the like. In some examples, one or more electrodes (e.g., reference electrode or measurement electrode) may be integrated with an input mechanism of the device (e.g., a rotatable input device, a depressible input device, or a depressible and rotatable input device, for example), as shown in FIG. 1B. One or more electrical signals measured by the one or more measurement electrodes can be measured and processed as described in more detail herein.

Figure 2A:
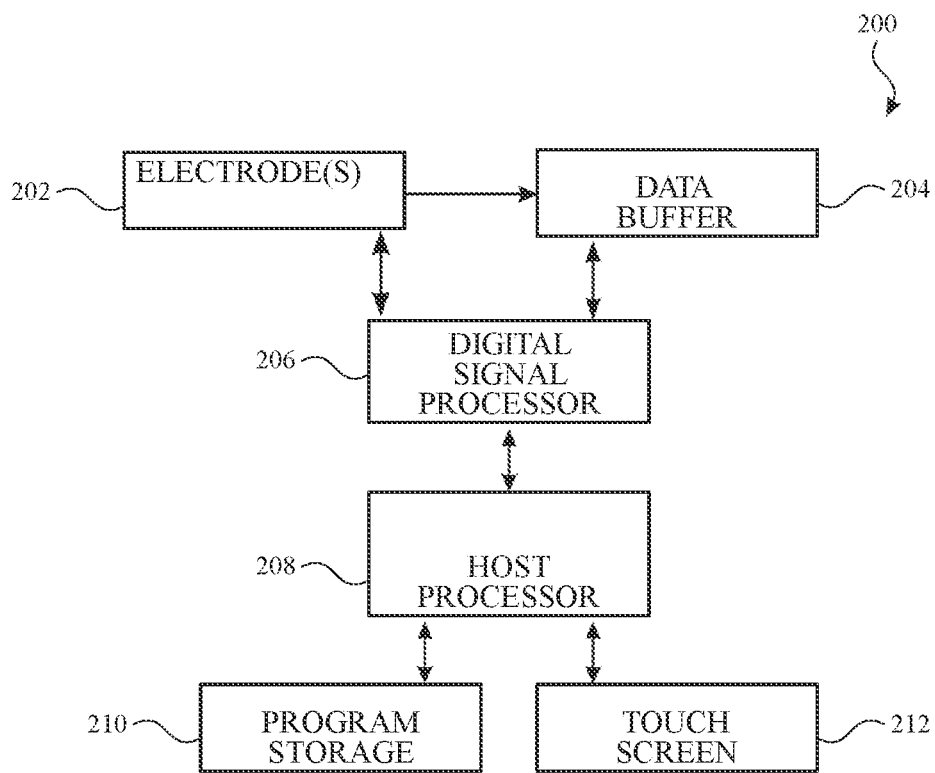
FIG. 2A illustrates a block diagram of an example computing system that illustrates one implementation of signal processing according to examples of the disclosure.

FIG. 2A illustrates a block diagram of an example computing system 200 that illustrates one implementation of signal processing to detect whether a device is submerged in water using digital signal processor 206 according to examples of the disclosure. Computing system 200 can be included in, for example, wearable device 150 or any mobile or non-mobile, wearable or non-wearable computing device. Computing system 200 can include digital signal processor 206 configured to detect submersion or to differentiate between user contact from water submersion using one or more criteria. Computing system 200 can also include one or more electrodes 202 to measure electrical impedance, data buffer 204 (or other volatile or non-volatile memory or storage) to store temporarily (or permanently) measurements from the one or more electrodes 202, host processor 208, program storage 210, and touch screen 212 to perform display operations (e.g., to display notification of water submersion). In some examples, touch screen 212 may be replaced by a non-touch sensitive display.

Host processor 208 can be connected to program storage 210 to execute instructions stored in program storage 210 (e.g., a non-transitory computer-readable storage medium). Host processor 208 can, for example, provide control and data signals to generate a display image on touch screen 212, such as a display image of a user interface (UI). Host processor 208 can also receive outputs from DSP (digital signal processor) 206 (e.g., measurements from one or more electrodes 202) and performing actions based on the outputs (e.g., activate water-related modes of the wearable device 150, provide haptic feedback, etc.). In some examples, when it is determined the wearable device 150 is not submerged in water, the host processor 208 can also receive outputs (touch input) from touch screen 212 (or a touch controller, not-shown). The touch input can be used by computer programs stored in program storage 210 to perform actions that can include, but are not limited to, adjusting control settings, viewing a menu, making a selection, executing instructions, and/or the like. Host processor 208 can also perform additional functions that may not be related to touch processing and display.

Note that one or more of the functions described herein, including contact and/or submersion detection and the processing of electrode measurements, can be performed by firmware stored in memory (e.g., in DSP 206) and executed by one or more processors (in DSP 206), or stored in program storage 210 and executed by host processor 208. The firmware can also be stored and/or transported within any non-transitory computer-readable storage medium for use by or in connection with an instruction execution system, apparatus, or device, such as a computer-based system, processor-containing system, or other system that can fetch the instructions from the instruction execution system, apparatus, or device and execute the instructions. In the context of this document, a "non-transitory computer-readable storage medium" can be any medium (excluding signals) that can contain or store the program for use by or in connection with the instruction execution system, apparatus, or device. The computer-readable storage medium can include, but is not limited to, an electronic, magnetic, optical, electromagnetic, infrared, or semiconductor system, apparatus or device, a portable computer diskette (magnetic), a random access memory (RAM) (magnetic), a read-only memory (ROM) (magnetic), an erasable programmable read-only memory (EPROM) (magnetic), a portable optical disc such a CD, CD-R, CD-RW, DVD, DVD-R, or DVD-RW, or flash memory such as compact flash cards, secured digital cards, USB memory devices, memory sticks, and the like.

The firmware can also be propagated within any transport medium for use by or in connection with an instruction execution system, apparatus, or device, such as a computer-based system, processor-containing system, or other system that can fetch the instructions from the instruction execution system, apparatus, or device and execute the instructions. In the context of this document, a "transport medium" can be any medium that can communicate, propagate or transport the program for use by or in connection with the instruction execution system, apparatus, or device. The transport medium can include, but is not limited to, an electronic, magnetic, optical, electromagnetic or infrared wired or wireless propagation medium.

It is to be understood that the computing system 200 is not limited to the components and configuration of FIG. 2A, but can include other or additional components (or omit components) in multiple configurations according to various examples. For example, sensing circuitry (e.g., corresponding to physiological signal sensor(s) 160) including an analog front end and an analog-to-digital converter (ADC) may be added between electrodes 202 and DSP 206 to convert the signals to the digital domain. As another example, touch screen 212 can be omitted. As yet another example, the ECG signal or other information from the analysis and processing can be relayed to another device (e.g., a tablet, laptop, smartphone, computer, server, etc.) via wired or wireless connection that can include a display or other feedback mechanism for outputting a visual representation of the data or other notifications or information. Additionally, the components of computing system 200 can be included within a single device, or can be distributed between multiple devices.

Returning back to digital signal processor 206, the wearable device 150 (or other device) may comprise one or more of measurement electrodes and one or more reference electrodes. Digital signal processor 206 can determine whether the wearable device 150 is in contact with the user's skin, submerged in water, or none of the above using measurements from the one or more of measurement electrodes and one or more reference electrodes. In some examples, an output voltage can be measured from the one or more electrodes and DSP 206 can calculate, from the output voltage, characteristics such as amplitude and phase of the output signal. These characteristics can be used to determine whether the wearable device 150 is in contact with the user's skin, submerged in water, or none of the above. It should be understood that although a DSP is described, other processing circuits could be used to implement the analysis and processing described herein including a microprocessor, central processing unit (CPU), programmable logic device (PLD), and/or the like.

Figure 2B:
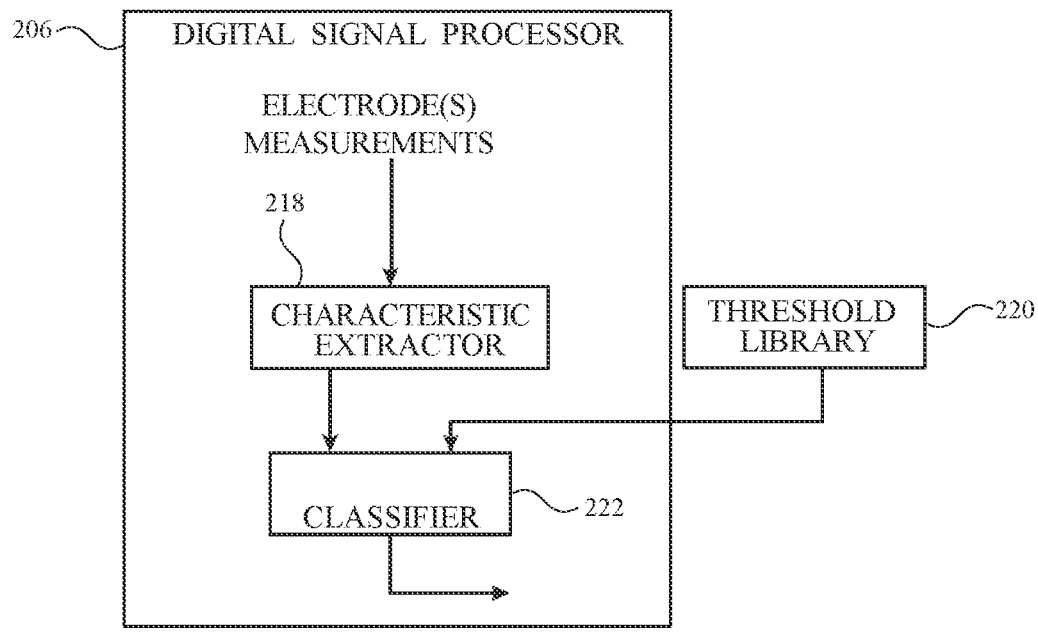
FIG. 2B illustrates processing circuitry for analysis and classification of signals according to examples of the disclosure.

FIG. 2B illustrates processing circuitry for analysis and classification of electrode measurements according to examples of the disclosure. The processing circuitry can be a digital signal processor 206 (e.g., corresponding to digital signal processor 206 in FIG. 2A). Digital signal processor 206 can receive signals from the one or more electrodes (e.g., electrode(s) measurements) from the measurement electrodes 202 directly or from data buffer 204. DSP 206 can include a characteristic extractor 218 and a classifier 222 implemented in hardware, software, firmware or any combination thereof, including one or more signal processing and/or application specific integrated circuits.

In some examples, the characteristic extractor 218 can be configured to extract one or more characteristics for the electrode measurements. The one or more characteristics optionally include amplitude and/or phase. In some examples, the classifier 222 is included to classify the electrode measurements based on comparisons with one or more predefined thresholds from threshold library 220. The threshold library 220 can include predefined thresholds such as one or more threshold amplitude characteristics and one or more threshold phase characteristics. The one or more threshold amplitude characteristics can be determined using empirical measurement of amplitude characteristics of the electrode measurements observed when the electrodes are in contact with the user's skin, submerged in water (or other fluids), or neither in contact nor submerged. Thus, the thresholds can be used to classify the state of the device using the amplitude measurement of the electrode measurements. The one or more threshold phase characteristics can be determined using empirical measurement of phase characteristics of the electrode measurements observed when the electrodes are in contact with the user's skin, submerged in water (or other fluids), or neither in contact nor submerged. Thus, the thresholds can be used to classify the state of the device using the phase measurement of the electrode measurements. In some examples, classifier 222 receives the amplitude and phase characteristics from characteristic extractor 218 and the predefined thresholds from the threshold library 220, and then outputs a classification of the state of the device as in contact with the user's skin, submerged in water, or neither in contact nor submerged.

In some examples, the classification as in contact, submerged, or neither in contact nor submerged is optionally assigned a confidence label representing the confidence in the classification. In some examples, classifier 222 provides a predicted classification as a probability. In some examples, the classification is the maximum of the probabilities for submerged, contact, or neither. In some examples, when the probability of the output voltage predicted to be submerged is above a threshold, then the output voltage is optionally classified as submerged, and when the probability of the output voltage predicted to be in contact is above the threshold, then the output voltage is optionally classified as in contact. In some examples, electrode measurements that cannot be reliably classified can be optionally designated unclassified or default to neither contact nor submerged classification. For example, when the probability of the electrode measurements are below the threshold, then the wearable device is labeled unclassified (e.g., none of the following: in contact, submerged, or neither contact nor submerged) or classified as neither contact nor submerged.

Figure 3A:
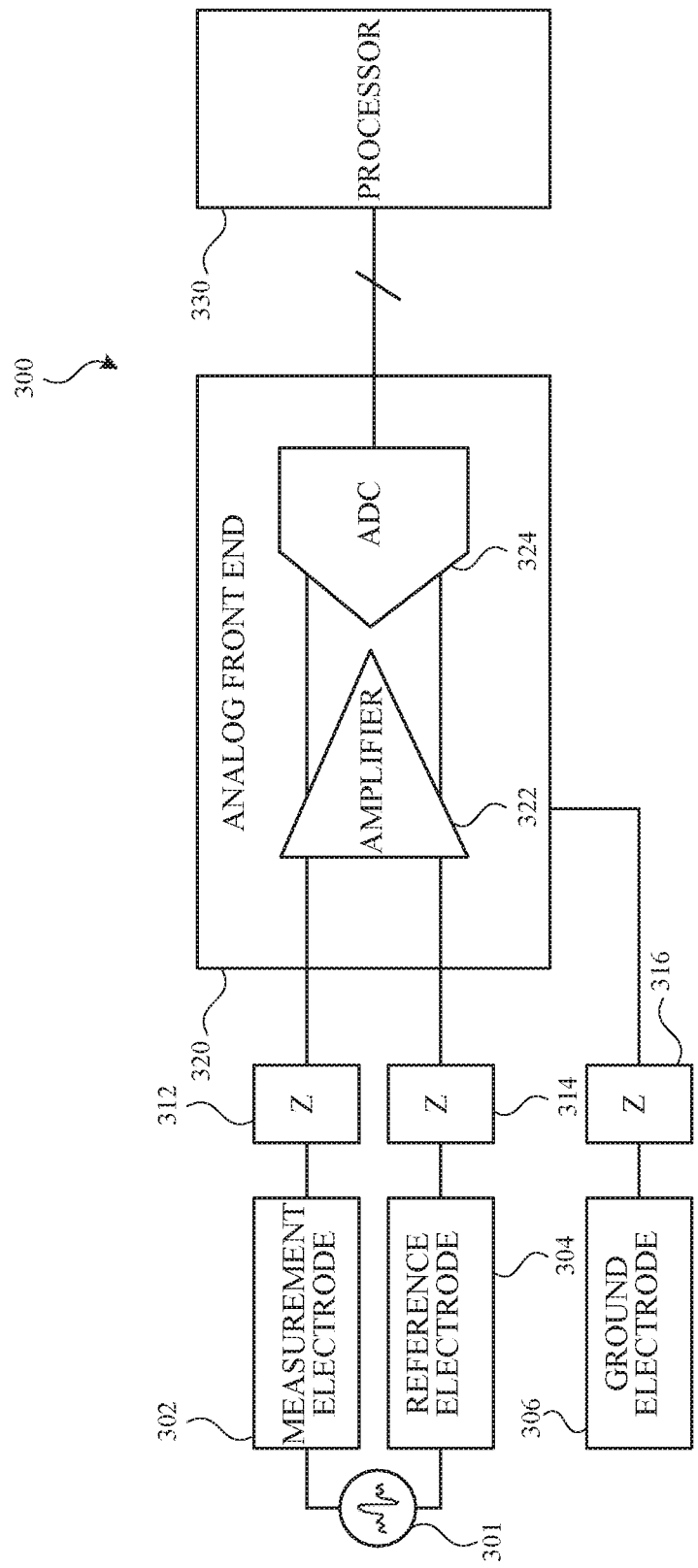
FIGS. 3A-3B illustrate example systems for measuring physiological signals according to examples of the disclosure.
Figure 3B:
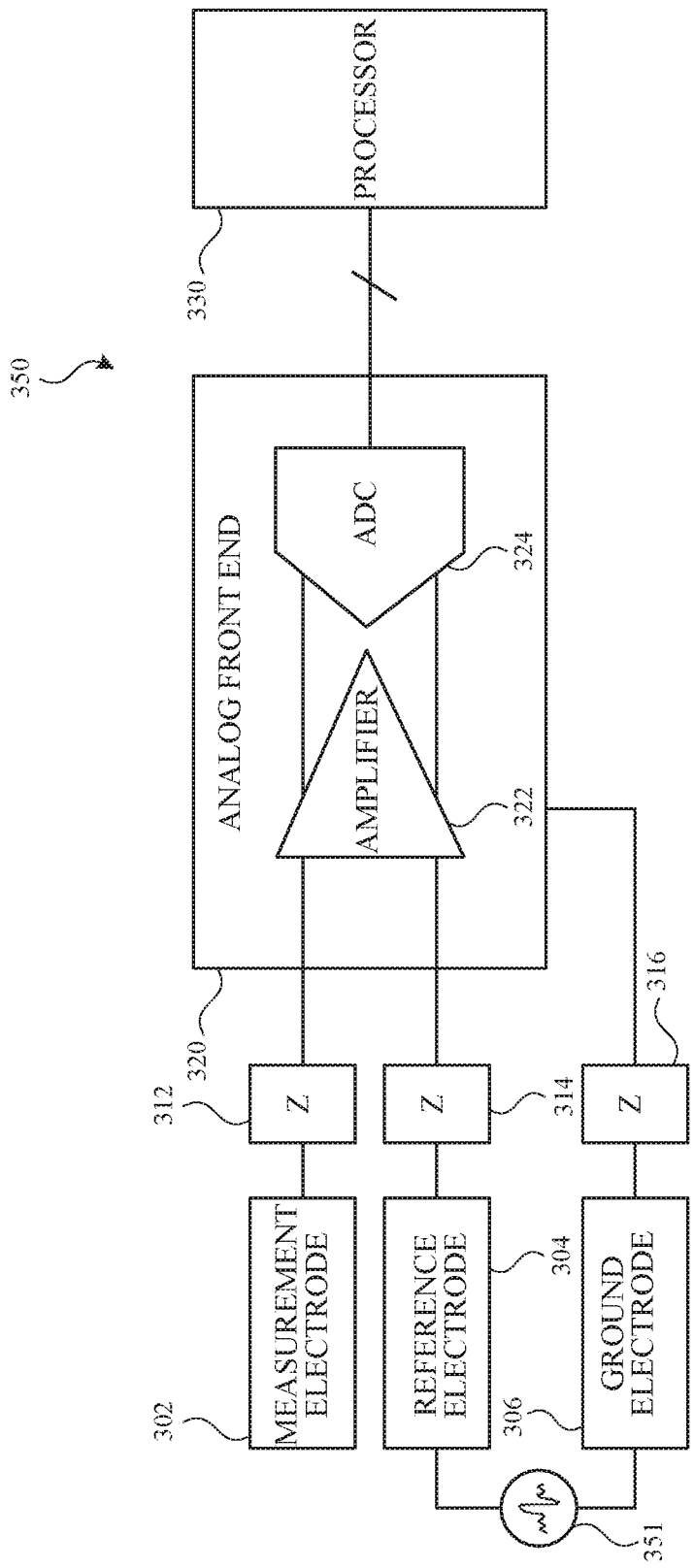

As described herein, a device can include a systems for measuring physiological signals, the reliability of which may depend on contact conditions. FIGS. 3A-3B illustrate example systems for measuring physiological signals according to examples of the disclosure. In FIG. 3A, circuit 300 can include processor 330 (e.g., corresponding to DSP 206 and/or host processor 208), analog front end 320, measurement electrode 302 (e.g., corresponding to measurement electrode 166C), reference electrode 304, and ground electrode 306 (e.g., corresponding to reference electrode 166A and reference electrode 166B). In some examples, circuit 300 resides on a mobile device (e.g., a wearable device 150). In some examples, analog front end 320 includes amplifier 322 and analog-to-digital converter (ADC) 324. Amplifier 322 can be a differential amplifier coupled to measurement electrode 302 (e.g., on the inverting input or on the non-inverting input) and to reference electrode 304 (e.g., on the non-inverting input or on the inverting input). In some examples, ground electrode 306 can be coupled to analog front end 320 to provide a shared ground reference between circuit 300 and ground electrode 306 (e.g., ground electrode 306 can provide a system ground reference voltage). In some examples, circuit 300 can include networks 312, 314, and 316, along the signal paths for the measurement electrode 302, reference electrode 304, and ground electrode 306, respectively. In some examples, networks 312, 314, and 316 can include circuit components (e.g., resistors, capacitors, inductors and/or diodes) and/or can include impedances inherent in circuit 300 (e.g., routing impedances, parasitic impedances, etc.). In some examples, networks 312, 314 and 316 can provide electrostatic discharge (ESD) protection for the circuit 300 and/or provide safety by limiting or preventing electrical currents being applied to the user's skin and/or preventing unexpected or unintentional external signals from entering the device and causing damage. In some examples, amplifier 322 can output an amplified differential signal and analog-to-digital converter 324 can convert the amplified differential signal into a digital signal. In some examples, amplifier 322 can output an amplified single-ended output. In some examples, the output of analog-to-digital converter 324 can be a multi-bit signal (e.g., 8 bits, 12 bits, 24 bits, etc.) coupled to processor 330. The multi-bit signal can be transmitted from analog front end 320 to processor 330 serially or in parallel. In some examples, analog-to-digital converter 324 can be a differential analog-to-digital converter and convert a differential analog input to a digital output. In some examples, analog-to-digital converter 324 can be single-ended and convert a single-ended analog input to a digital output. In some examples, differential amplifier 322 can be implemented with two single-ended amplifiers and ADC 324 can be implemented with two ADCs (each connected to the output of one of the single-ended amplifiers).

In some examples, a user can wear the wearable device including circuit 300. In such examples, reference electrode 304 and ground electrode 306 can be in contact with the wrist of the user. When a user touches measurement electrode 302 (e.g., electrode 166C on crown 162 of wearable device 150), measurement electrode 302 can receive a physiological signal from the user. In FIG. 3A, the user is represented as physiological signal source 301. In some examples, when the user touches measurement electrode 302, a path can be created through physiological signal source 301 from measurement electrode 302 and reference electrode 304 and/or ground electrode 306 (e.g., from the user's finger across the user's chest to the wrist upon which the user is wearing the wearable device and to reference electrode 304 and/or ground electrode 306). In some examples, contacting measurement electrode 302 can cause circuit 300 to measure a physiological signal from physiological signal source 301.

FIG. 3B illustrates an example circuit diagram in which a user of the device contacts the housing of the wearable device instead of a measurement electrode. In FIG. 3B, circuit 350 can include the same components as circuit 300, the description of which is omitted for brevity. In some examples, when the user touches the housing of the wearable device, an alternative path can be created through physiological signal source 351 from reference electrode 304 (e.g., electrode 166A connected to the user's wrist) and ground electrode 306 (e.g., the housing of the wearable device can be grounded to system ground via ground electrode 306). In some examples, the alternative path can cause physiological signal source 351 to inject a physiological signal between reference electrode 304 and ground electrode 306. In some examples, the physiological signal can cause amplifier 322 to detect and amplify a physiological signal. In such examples, processor 330 may misinterpret the signal from the physiological sensor(s) as a proper physiological signal. However, the resulting physiological signal can be attenuated, unstable, or otherwise unreliable.

Figure 4A:
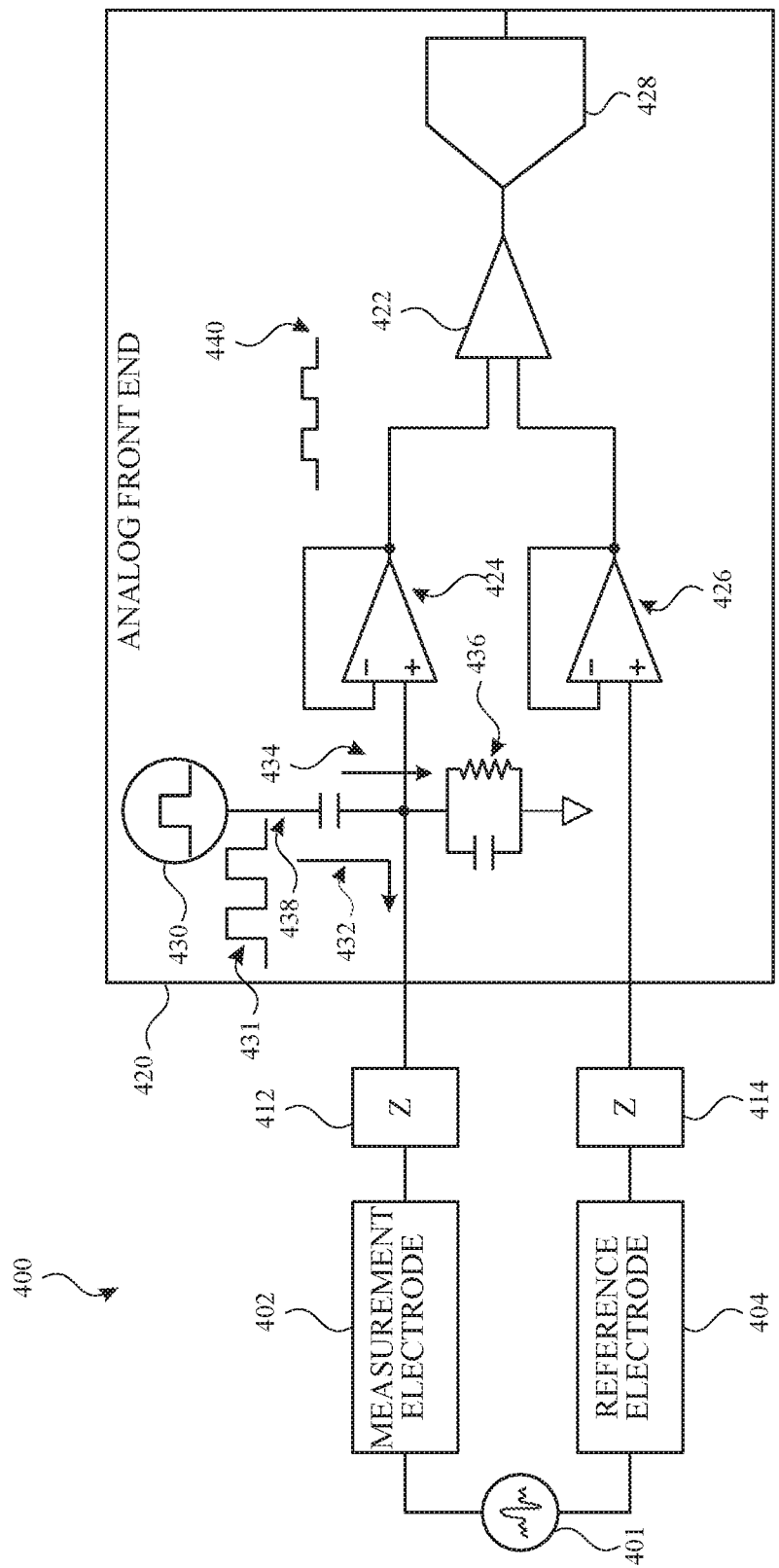
FIGS. 4A-4B illustrate example systems for measuring physiological signals and for contact detection according to examples of the disclosure.
Figure 4B:
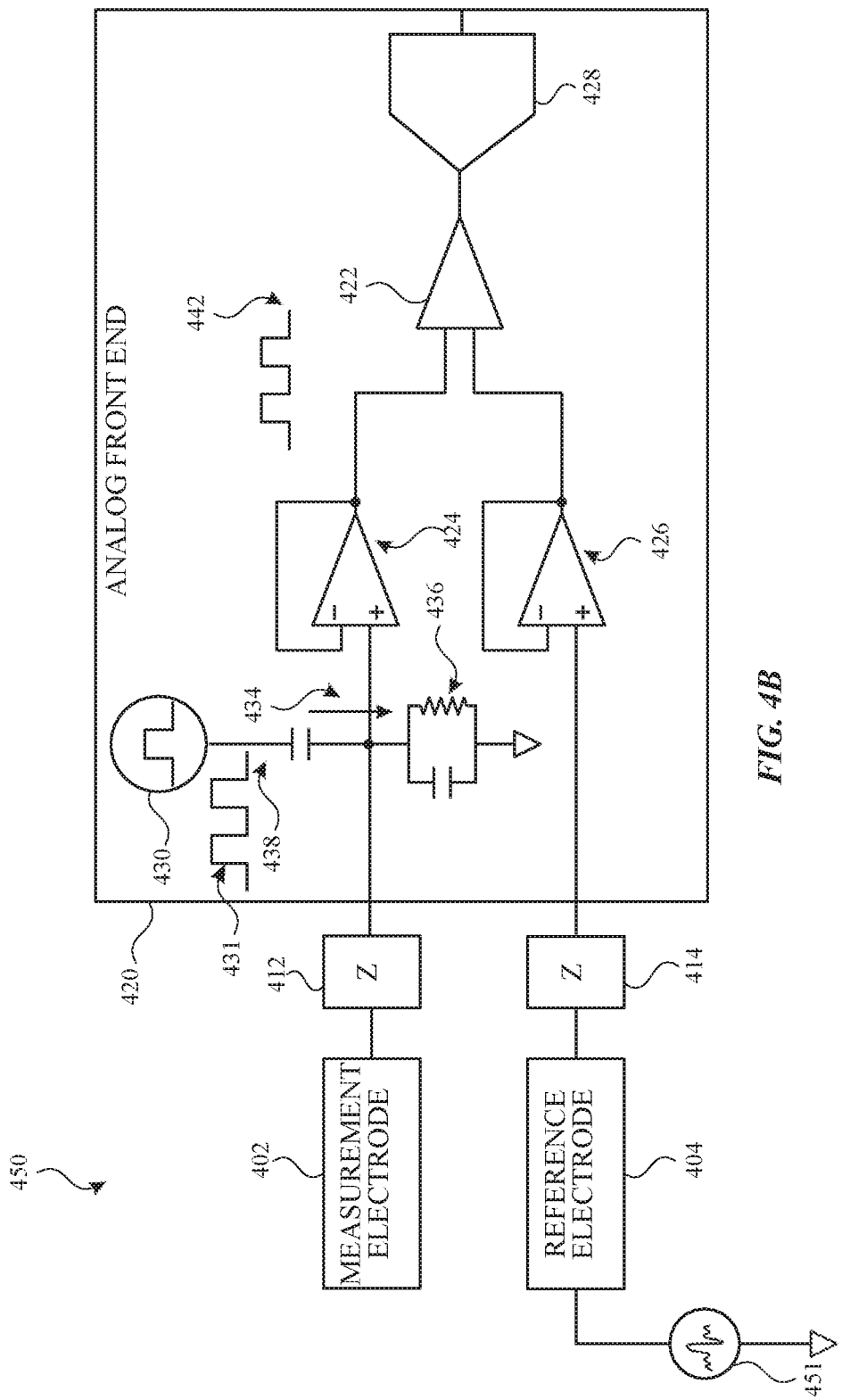

FIGS. 4A-4B illustrate example systems for measuring physiological signals and for contact detection according to examples of the disclosure. For ease of description, FIGS. 4A-4B focus on a measurement electrode, a reference electrode and the analog circuitry for measuring physiological signals and for contact detection, processing circuitry, and a ground reference electrode are not illustrated. In FIG. 4A, circuit 400 can include analog front end 420, measurement electrode 402 (e.g., corresponding to measurement electrode 166C) and reference electrode 404 (e.g., corresponding to reference electrode 166A and/or reference electrode 166B). Analog front end 420 can include amplifier 422 (e.g., similar to amplifier 322), analog-to-digital converter 428 (e.g., similar to ADC 324), buffers 424 and 426, and test signal circuitry. In some examples, buffers 424 and 426 can provide an impedance matching interface for the electrodes (e.g., matching the impedance of the user's body contacting with the respective electrode). In some examples, buffer 424 and 426 can be designed to accommodate the large input impedances 412, 414 between the electrodes and the buffer 424 and 426. In some examples, buffer 424 and 426 can be designed to reduce noise or interference from the input networks that may enter inputs to amplifier 422.

In some examples, the test signal circuitry (e.g., stimulation circuit) can include test signal generator 430 and capacitor 438. In some examples, test signal generator 430 can be a square wave generator, a clock generator, a periodic signal generator or other suitable signal generator. In some examples, test signal generator can include a digital to analog converter (DAC) to convert a digital signal into an analog stimulation signal. Test signal 431 (e.g., stimulation signal) generated by test signal generator 430 can be a square wave, a sine wave, a trapezoidal wave, a saw-tooth wave or any other suitable periodically oscillating, non-oscillating or non-periodic (e.g., pseudo-noise signal) waveform. The test signal, regardless of waveform, can be known or predetermined to the system to enable detection of the resulting measured test signal, in some examples as described herein. Test signal 431 can be capacitively coupled via capacitor 438 to measurement electrode 402. In some examples, test signal generator 430 can be controlled by a processor (e.g., DSP 206, host processor 208, processor 330). In some examples, the processor can change the frequency and/or amplitude of test signal 431 and/or enable and disable test signal generator 430. In some examples, the test signal generator 430 can be a clock output of processor 330.

In some examples, analog front end 420 can include an impedance network 436. In some examples, impedance network 436 can be one or more discrete capacitors and/or one or more discrete resistors. In some examples, impedance network 436 can represent parasitic impedances in the system. In some examples, impedance network 436 can be one or more capacitors (including respective parasitic impedances). In some examples, capacitor 438 and impedance network 436 form a voltage divider through path 434 to ground and test signal 431 generated by test signal generator 430 can be divided by the voltage divider. Buffer 424 can measure a node between capacitor 438 and impedance network 436. The resulting measured test signal can be used to detect contact on measurement electrode 402.

In some examples, the amplitude (e.g., voltage level) of the measured test signal can depend on the load experienced by the test signal. For example, when a user touches measurement electrode 402, the resulting measured test signal can be attenuated. As illustrated in FIG. 4A, contact between a user (e.g., a finger) and measurement electrode 402 can form a path 432 for test signal 431. In some examples, path 432 can be formed through physiological signal source 401 (e.g., the body of the user) to system ground via the ground electrode (e.g., ground electrode 306 contacting the user's wrist). In some examples, a user can be contacting measurement electrode 402 with a first finger (e.g., an index finger) and the housing of the device with a second finger (e.g., a thumb). In such cases, path 432 for test signal 431 can be formed through physiological signal source 401 (e.g., the body of the user) to system ground through the finger touching the housing of the device (e.g., the housing of the device can be grounded to system ground). Thus, path 432 can form an impedance in parallel to path 434 (through impedance network 436) and change the loading experienced by test signal 431. In such examples, the resulting measured test signal 440 at buffer 424 can be attenuated. In contrast, when a user is not touching measurement electrode 402 (or is contacting the housing), the resulting measured test signal may not be attenuated (or may be attenuated less). As illustrated in FIG. 4B, without contact on measurement electrode 402, path 432 may not be formed to system ground. Without path 432 to system ground for test signal 440, the resulting measured test signal 442 may not be attenuated (or may be attenuated less) than expected from the voltage divider of capacitor 438 and impedance network 436. Comparing the amplitude of resulting measured test signals 440 and 442, measured test signal 440 corresponding to contact on measurement electrode 402 can be more attenuated than measured test signal 442. In some examples, test signal 431 can travel through path 432, through physiological signal source 401, and into reference electrode 404 and can be detected by buffer 426. In some examples, detection of the resulting test signal by buffer 426 can be sufficient to determine that a user is contacting with measurement electrode 402. In some examples, a differential measurement can be performed on the resulting signal detected by buffer 426 and the resulting signal detected by buffer 424 to determine the amplitude level of the resulting test signal. In some examples, a single-ended measurement can be performed to determine the amplitude of the resulting test signal (e.g., without using reference electrode 404 and buffer 426).

In some examples, the response of test signal 431 to the load can depend on the frequency of test signal 431 and the respective impedance of the signal paths. In some examples, the frequency of test signal 431 can be varied to determine the load of the signal paths at the respective frequency (e.g., the quality of the skin-to-electrode connection as a function of the test signal frequency can be determined). In some examples, an initialization process can be used to select a frequency for differentiating between when measurement electrode 402 is contacted and when it is not contacted (e.g., a frequency for test signal 431 that results in an observable change in resulting test signal amplitude). In some examples, test signal 431 can include a plurality of frequencies concurrently (e.g., test signal 431 can include multiple frequency components). In such an example, the reactance of the system to different frequencies can be determined at one time.

A threshold amplitude (e.g., voltage level) can be used to determine whether measurement electrode 402 is contacted. When the measured test signal is less than a threshold amplitude, the system (e.g., DSP 206, host processor 208, processor 330) can determine that the measurement electrode is contacted (e.g., sufficient skin-to-electrode coupling exists for high-quality physiological measurements). When the measured test signal is greater than or equal to the threshold amplitude, the system can determine that the measurement electrode is not contacted (or that the housing is contacted, or that there is insufficient skin-to-electrode coupling for a high-quality physiological measurement). The threshold amplitude can be set, for example, based on empirical study of expected range of load impedance from skin-to-electrode coupling. Additionally, the threshold amplitude can be set based on other factors including accuracy of the resulting waveform and the desired sensitivity (e.g., with respect false positives). As described herein, detecting contact with the measurement electrode can be used to differentiate between a reliable measured physiological signal from an unreliable measured physiological signal. In some examples, the system can provide a notification for the user to contact the measurement electrode to begin measuring a physiological signal. In some examples, as described herein, contact detection can be used as a trigger to begin physiological signal measurements and/or as a trigger to end physiological signal measurements. In some examples, contact detection can be used to assign a confidence to physiological signal during a measurement session. In some examples, beginning physiological signal measurements can include acquiring the physiological signal (e.g., by data buffer 204 and/or DSP 206), storing the physiological signal (e.g., in program storage 210) and/or displaying the physiological signal on the display. In some examples, when the system determines that the measurement electrode is not contacted, the system can forego measuring the physiological signal (e.g., powering down the circuit, discarding the physiological signal measurements, or otherwise not process incoming signals). In some examples, when the system determines that the measurement electrode is not contacted, the system can still measure the physiological signal, but with a low confidence value indicative that the physiological signal is low-quality (e.g., may not be reliable for one or more intended uses). In some examples, the low confidence can be represented in a binary manner (e.g., a low-confidence/low-quality flag can be set). In some examples, the confidence can be represented in another manner (e.g., a probability) representative of the quality. In some examples, when the confidence is below a threshold or when the low-confidence/low-quality flag is set, a notification can be presented to the user to indicate that the measured physiological signal measurement may be unreliable or low quality (e.g., display the physiological signal with a visual indicator, display a notification on the display of the device and/or any other visual feedback, and/or an audio feedback and/or a haptic feedback and/or any other suitable feedback mechanism).

In some examples, when a user contacts measurement electrode 402, a physiological signal from physiological signal source 401 can enter circuit 400. In some examples, the physiological signal can be mixed or otherwise added to test signal 431 generated by test signal generator 430. In some examples, the frequency of test signal 431 can be higher than the frequency of physiological signal. For example, the frequency spectrum of a physiological signal can be between 0.5 Hz to 40 Hz and the frequency of test signal 431 can be 100 Hz, 135 Hz, 200 Hz, 250 Hz, 400 Hz, 500 Hz, 600 Hz, or any other suitable frequency above 40 Hz. In some examples, the frequency spectrum of a physiological signal can be between 0 Hz to 150 Hz and the frequency of test signal 431 can be 500 Hz, 600 Hz, or any other suitable frequency above 150 Hz. In some examples, the amplitude of test signal 431 can be smaller than the amplitude of the physiological signal. In such examples, the physiological signal can act as a carrier wave for test signal 431 (e.g., in a manner similar to amplitude modulation). In some examples, a filter (e.g., a high-pass filter or a band-pass filter) can be used to filter the physiological signal and leave the test signal (e.g., test signal 440) to be compared against the threshold to determine whether measurement electrode 402 is contacted.

In some examples, after contact with measurement electrode 402 is determined, test signal generator 430 can stop generating test signal 431. In such examples, stopping test signal generation can save power and/or reduce or eliminate the need for filtering (of the test signal from the physiological signal). In some examples, even after contact with measurement electrode 402 is determined, test signal generator 430 continues providing test signal 431. In such examples, a filter (e.g., a low-pass filter or band-pass filter) can be used to filter test signal 431 and leave the physiological signal for measurement and/or processing. In some examples, continuing to generate test signal 431 can allow the system (e.g., DSP 206, host processor 208, processor 330) to continue to determine that the user is contacting measurement electrode 402. In some examples, when the user of the device stops contact with measurement electrode 402, the system can determine that contact has stopped and cease measuring and/or processing the physiological signal. In some examples, the system can provide a notification to the user regarding the termination of contact with the measurement electrode during a physiological signal measurement session. In some examples, test signal generation can be periodically restarted to determine whether measurement electrode 402 is contacted. In some examples, contact detection can be continuous (e.g., the test signal can be generated at all times), periodic (e.g., generated once a second, once a minute, once an hour), or may be generated in response to a trigger (e.g., launching a physiological signal application, beginning a physiological signal measurement session, while a wearable device is determined to be worn, etc.).

Although FIGS. 4A-4B illustrate the integration of the test signal circuitry with the physiological signal measurement circuitry, it is understood that test signal circuitry can be implemented in a different manner. For example, the test signal circuitry can include an amplifier or other front end circuitry (e.g., separate from amplifier 422, etc.) to perform the functions of measuring the test signal and performing contact detection. In some examples, separate signal paths can be used for contact detection and physiological sensing (e.g., not integrating the test signal circuitry with the physiological signal measurement circuitry). In some examples, implementing contact detection and physiological sensing separately can allow for optimization of the circuitry for contact detection for the frequencies, signal range and/or signal precision of the test signal for contact detection and optimization of the circuitry for the frequencies, signal range and/or signal precision for physiological sensing. In some examples a switching circuit can be provided to couple the test signal circuitry (e.g., test signal generator and measurement amplifier) to the measurement electrode during contact detection and to decouple the measurement electrode from the test signal circuitry during the physiological signal measurement. In some examples, the test signal circuitry can be integrated with saturation detection circuitry, as will be described below. Additionally, although illustrated as a discrete source in FIG. 4A-4B, test signal 431 can be generated by a processor (e.g., DSP 206, host processor 208). In some examples, the same processor can also be coupled to receive the measured test signals from the output of buffer 424 or another buffer or amplifier circuit.

Furthermore, although FIGS. 4A-4B illustrate the integration of the test signal circuitry onto the signal path of measurement electrode 402, it is understood that similar test signal circuitry can be integrated onto the signal path of reference electrode 404 to detect contact between the user (e.g., wrist) and reference electrode 404 in a similar manner. Additionally, although FIGS. 4A-4B illustrate one measurement electrode 402 and one reference electrode 404, in some examples, the system can have a plurality of measurement electrodes and/or a plurality of reference electrodes, and similar test signal circuitry can be integrated with some or all of these electrodes.

Figure 4C:
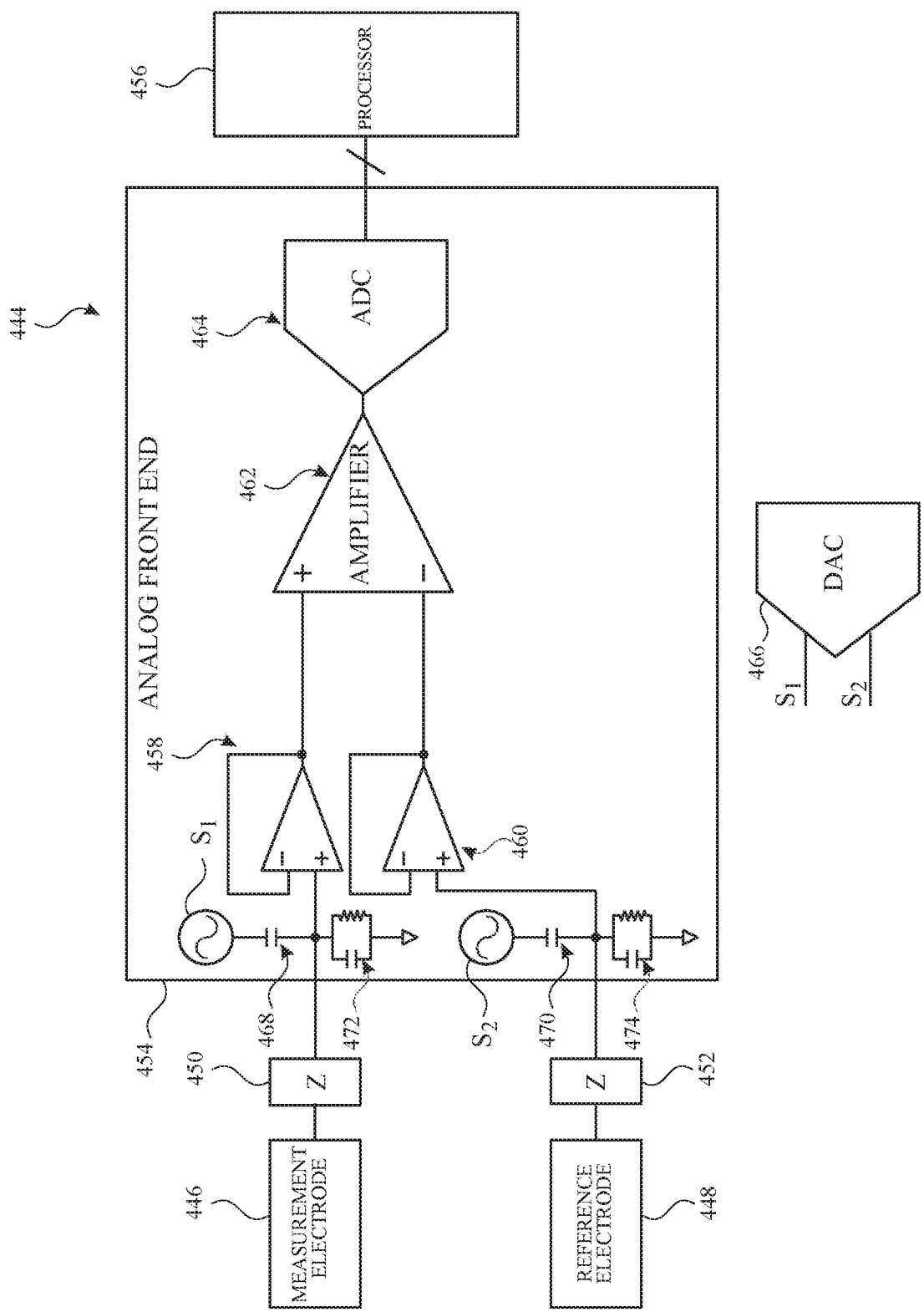
FIG. 4C illustrates an example system for measuring physiological signals and for contact detection on multiple electrodes according to examples of the disclosure.

In some examples, contact detection can be performed for multiple electrodes by driving a first stimulation signal on one of the electrodes (e.g., a first measurement electrode) and a second stimulation signal on a second of the electrodes (e.g., a second measurement electrode or a first reference electrode). Contact detection on multiple electrodes can be used to improve performance of physiological signal detection for systems including proper contact on two electrodes in a similar manner as described above for contact detection on one measurement electrode 402. FIG. 4C illustrates an example system for measuring physiological signals and for contact detection on multiple electrodes according to examples of the disclosure. Circuit 444 can be similar to circuit 400. Circuit 444 can include a first electrode (e.g., measurement electrode 446 corresponding to measurement electrode 402), a second electrode (e.g. reference electrode 448 corresponding to reference electrode 404), impedance networks 450 and 452 (e.g., corresponding to impedance networks 412 and 414), an analog front end circuit 454 (e.g., corresponding to analog front end 420) and a processor 456. Analog front end circuit 454 can include buffers 458 and 460 (e.g., corresponding to buffers 424 and 426), differential amplifier 462 (e.g., corresponding to amplifier 422), and ADC 464 (e.g., corresponding to ADC 428).

Circuit 444 can also include test signal circuitry. However, unlike the illustration of circuit 400, the test signal circuitry can include circuitry to drive a first stimulation signal on a first electrode and a second stimulation signal (different from the first stimulation signal) on a second electrode (different from the first electrode). For example, the test signal circuitry can include a test signal generator including a digital to analog converter (DAC) 466 configured to output two complementary stimulation signals, S1 and S2. For example, S1 and S2 can be sinusoidal waves of the same frequency with 180 degree phase shift between S1 and S2. In some examples, DAC 466 can receive an oscillating signal and/or digital values from a memory to generate voltage values for the waveforms of S1 and S2. The first stimulation signal can be driven onto the first electrode via capacitor 468 and the second stimulation signal can be driven onto the second electrode via capacitor 470.

It should be understood that although S1 and S2 are described above as sinusoidal waves with a 180 degree phase shift, that in some examples, the first and/or second stimulation signals can be other waveforms (e.g., square wave, trapezoidal wave, saw-tooth wave or any other suitable wave), and/or the first and second stimulation signals can have a different phase relationship (e.g., 90 degree phase shift or any other suitable phase shift). Additionally, in some examples, the frequency of S1 and S2 can be the same or can be different (e.g., 1 kHz and 10 kHz). Finally, it should be understood that although DAC 466 is shown as generating both stimulation signals, that other circuitry can be used to generate the stimulation signals (two single-output DACs, or other test signal generator such as those described above with respect to FIGS. 4A-4B).

Circuit 444 can also include impedance networks 472 and 474 (e.g., similar to impedance network 436) that can form voltage dividers with capacitors 468 and 470 for the two electrodes. The voltage of respective stimulation signals S1 and S2 can be divided by the respective voltage divider. In some examples, impedance networks 472 and 474 can include one or more discrete capacitors and/or one or more discrete resistors, and/or can represent parasitic impedances for each of the electrodes (modeling the electrode interface).

Buffer 458 can measure the node between capacitor 468 and impedance network 472 corresponding to the first electrode (e.g., measurement electrode 446). Buffer 460 can measure the node between capacitor 470 and impedance network 474 corresponding to the second electrode (e.g., reference electrode 448). The output of buffers 458 and 460 can be input to the two input terminals of differential amplifier 462. The output of differential amplifier 462 can represent a combination of the voltage at the node of the first electrode and the voltage at the node of the second electrode. For example, due to the complimentary nature of S1 and S2, the output of differential amplifier 462 can represent the sum of the voltages output by buffers 458 and 460 (subject to phase shifts introduced by the impedance changes due to electrical system and contact between the user and the electrode). For other non-complimentary stimulation signals, the differential amplifier can still combine outputs of buffers 458 and 460. The resulting output from differential amplifier 462 can, in some examples, have a sinusoidal waveform. The analog output from differential amplifier 462 can be digitized by ADC 464 and the digitized values can be sent to processor 456 for contact detection. It should be understood that although circuit 444 illustrated in FIG. 4C shows differential amplifier 462, it is understood that in some examples, differential amplifier 462 can be replaced by two single-end amplifiers and two separate ADCs.

For example, in a similar manner as described above, contact between a user and the first electrode can attenuate the output of buffer 458 (with respect to the output without contact) and contact between the user and the second electrode can attenuate the output of buffer 460 (with respect to the output without contact). The composite signal output from amplifier 462 can be evaluated to determine whether it meets one or more criteria. The one or more criteria can include a criterion that requires (e.g., that is satisfied when) the composite signal detected in response to the first and second stimulation is less than a threshold. When the composite digitized output of amplifier 462 is less than a threshold, processor 456 can determine proper contact between the user and both of the electrodes (e.g., sufficient contact to generate a physiological signal of threshold quality). When the composite digitized output of amplifier 462 is greater than the threshold, processor 456 can determine at least one improper contact between the user and one of the electrodes (e.g., insufficient contact to generate a physiological signal of threshold quality). As a result of detecting the composite digitized output is less than a threshold (corresponding to proper contact at two electrodes), the system can measure the physiological signal and/or continue measuring the physiological signal. As a result of detecting the composite digitized output is greater than the threshold (corresponding to improper contact at one or two electrodes), the system can forgo measuring a physiological signal and/or stop measuring the physiological signal (or discard the results or present a notification to the user, etc.), in a similar manner as described herein for contact detection for one measurement electrode.

As described herein, in some examples, the stimulation signals for contact detection can be continuously applied, periodically applied or may be applied in response to a trigger. In some examples, the contact detection can be performed continuously to indicate the quality of a physiological signal measurement during physiological signal measurement. In some examples, the contact detection can be used to trigger a physiological signal measurement session and/or terminate a physiological signal measurement session. In some examples, the contact detection can be used to differentiate between intended contact with a measurement electrode (e.g., on crown 162) from unintended contact with the measurement electrode (e.g., from a user's wrist). For example, contact between crown 162 and the user's wrist may be relatively intermittent (e.g., less than 3-5 seconds) compared with intended input for a physiological signal measurement that may require a threshold duration of contact (e.g., greater than 10 seconds). Thus, a session started due to unintended wrist contact may be terminated (and/or the session results can be discarded rather than displaying an inaccurate physiological signal measurement).

In order to perform contact detection continuously, in some examples, the stimulation frequency can be selected to be outside the frequency band used for physiological signal measurement. For example, as discussed herein, in some examples, the frequency of the stimulation signal(s) can be higher than the frequency of physiological signal. For example, the frequency spectrum of a physiological signal can be less than 150 Hz and the frequency of stimulation signal(s) can be 500 Hz, 600 Hz, or any other suitable frequency above 150 Hz. Additionally, using a sine wave rather than a square wave for the stimulation signal can improve separation of the frequency bands (as a square wave includes frequency content in multiple frequency ranges).

The description of physiological signal measurement and contact detection in the context of FIGS. 3A-3B and 4A-4C primarily describes contact (or not) from the user's skin. However, as described herein, the submersion of the device can also be detected (e.g., using the same circuitry for physiological signal sensing and/or contact detection described above, or using similar circuitry applied to another electrode).

For example, the amplitude (e.g., voltage level) of the resulting test signal (e.g., at the output of buffers 424, 426, 458, or 460 can optionally be used to determine whether measurement electrode and/or reference electrode is in contact with the user's skin, submerged in water, or none of the above. In some examples, when water is present on or in the measurement electrode or reference electrode, the water creates a leakage path between the electrode to system ground and causes a drop in amplitude for similar reasons as described above as for skin contact.

Figure 5A:
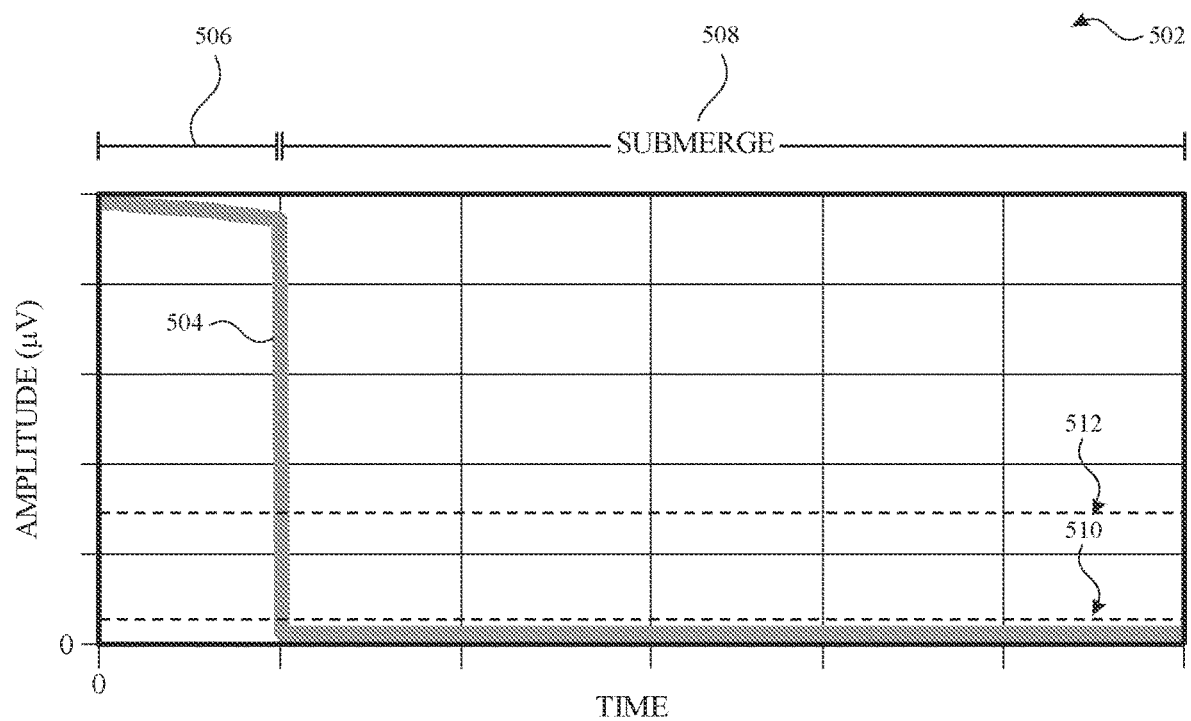
FIGS. 5A-5B illustrate example plots of signals according to examples of the disclosure.
Figure 5B:
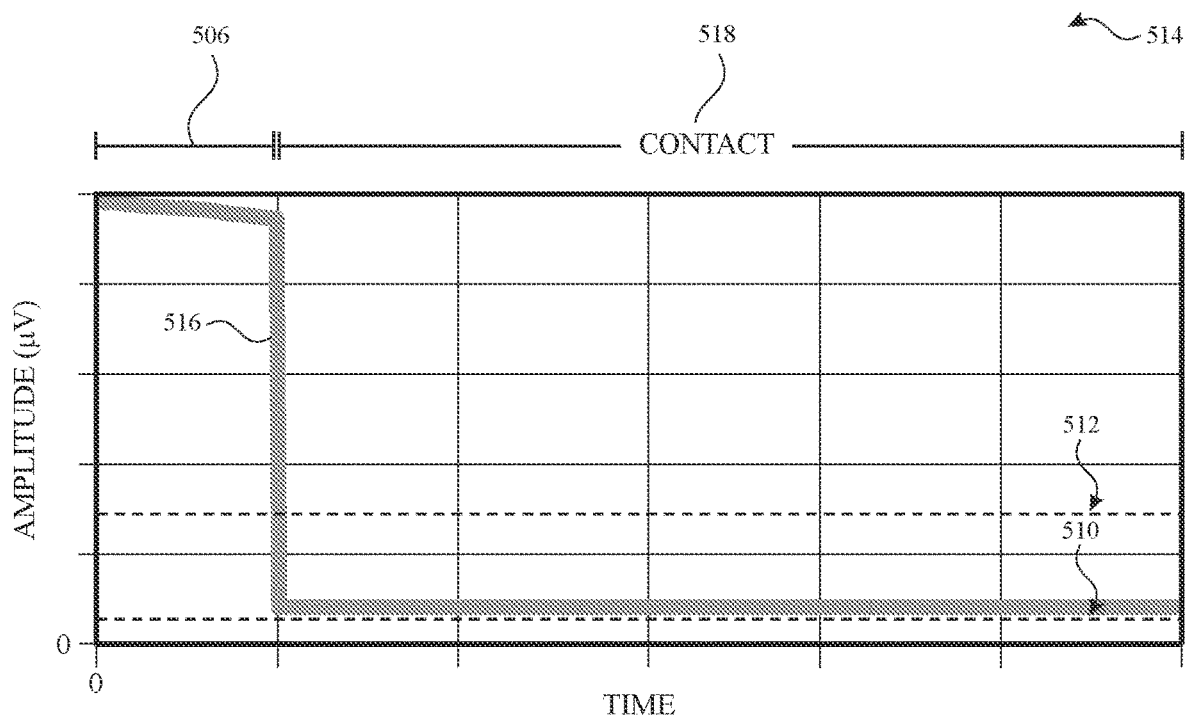

In some examples, the amount of amplitude drop due to water or due to contact can be different, and the difference in amplitude can be used to differentiate between the contact and submerged conditions. For example, FIGS. 5A-5B illustrate example plots of the amplitude characteristic of the output measured in response to the stimulation signals according to examples of the disclosure. Plot 502 illustrates an amplitude signal measurement during two periods, including a baseline period 506 (e.g., before contact) and a submerge period 508. Plot 514 also illustrates an amplitude signal measurement during two periods, including a baseline period 506 (e.g., before submersion) and a contact period 518. Plots 502 and 514 also include two threshold amplitude characteristics, including first threshold 510 and second threshold 512. As illustrated in plots 502 and 514, the amplitude signal measurements 504/516 drop as a result of contact or submersion. However, the difference in amplitude attenuation can be used to differentiate between the contact and submerged conditions. For example, when the amplitude is determined to be less than a first threshold amplitude (e.g., first threshold 510), the system (e.g., DSP 206, host processor 208) can determine that the measurement electrode is submerged (e.g., sufficient skin-to-electrode coupling exists). When the amplitude is greater than the first threshold amplitude (e.g., first threshold 510) and less than a second threshold amplitude (e.g., second threshold 512), the system can determine that the measurement electrode is contacted. When the amplitude is greater than the first and second threshold amplitudes, the system can determine that the measurement electrode is not contacted nor submerged. The first threshold amplitude and the second threshold amplitude can be determined, for example, based on empirical study of expected range of load impedance from skin-to-electrode coupling and under water submersion conditions.

As described herein, the amplitude characteristic of the measured test signal can be used to differentiate between contact, submergence, or none of the above. In some examples, when submergence is determined, the system can provide a notification for the user that submergence is detected and that a water mode for the wearable device 150 will be activated. Once water mode is activated, the system may be configured to initiate a process to disable capacitance sensing of the device, initiate a process to detect water related activity, and/or initiate a process to transition the touch screen to a force sensing mode. In some examples, once water mode is activated, the system may also forgo measuring the physiological signal, which may also be unreliable when submerged. In some examples, when the system determines submergence, the system can optionally change the rate of driving the stimulation signal on the measurement electrode 446 in FIG. 4C (or measurement electrode 402 in FIG. 4B or 4A), or otherwise contact and/or submergence detection scan can be performed less often (e.g., once per 10 seconds rather than once per 5 seconds). In some examples, when the system determines that the measurement electrode is neither contacted nor submerged, the system can optionally continue to perform the contact and/or submergence detection scan at the same rate (e.g., once per 5 seconds). In some examples, when water and/or moisture is detected, the system can optionally perform the contact and/or submergence detection scan at an increased rate (e.g., once per 3 seconds) relative to the rate before water and/or moisture is detected. In some examples, when submergence is detected, the system can optionally forego or cease performing the contact and/or submergence detection scan.

In some examples, after determining that the measurement electrode is submerged, test signal generator 430 can stop generating test signal 431 (e.g., for a threshold period of time or until user input is received indicating the device is no longer submerged). In such examples, stopping test signal generation can save power. In some examples, even after submergence is determined, test signal generator 430 continues providing test signal 431 but less often (e.g., once every 10 seconds, 15 seconds, 20 seconds, 25 seconds, 30 seconds, or 1 minute). In some examples, continuing to generate test signal 431 can allow the system (e.g., DSP 206, host processor 208) to continue to determine that the measurement electrode 402 is submerged. In some examples, when the with measurement electrode is no longer submerged (e.g., de-submerged), the system can determine that submergence has stopped and cease functioning in the water mode (e.g., revert the process related to disabling capacitance sensing of the device, cease detection of water related activity, and/or transition back to (enable) the touch screen). In some examples, the system can optionally provide a notification to the user regarding de-submergence of the wearable device. In some examples, contact or submergence detection can be continuous (e.g., the test signal can be generated at all times), periodic (e.g., generated once every 1 second, once every 3 seconds, once every 5 seconds, once every 7 seconds, once a minute, once an hour), or may be generated in response to a trigger (e.g., launching a water-related application, beginning a water-related activity session, while a wearable device is determined to be worn, etc.).

Figure 6A:
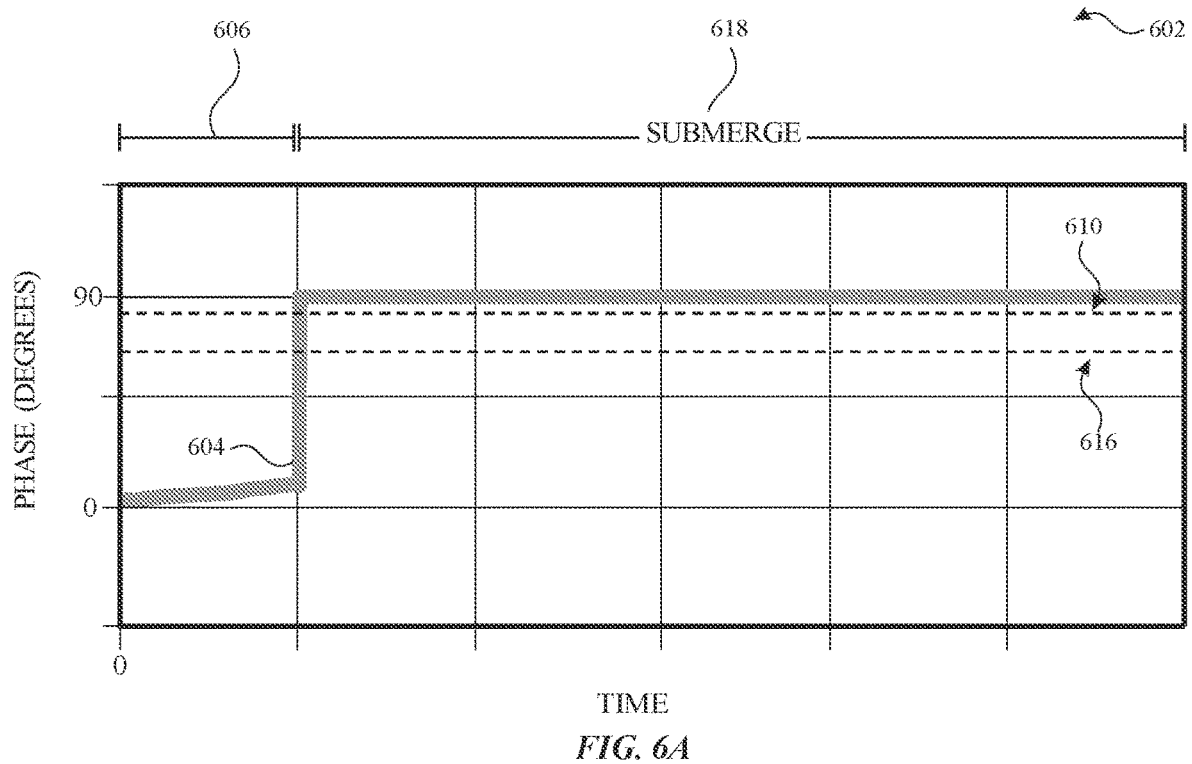
FIGS. 6A-6B illustrate example plots of signals according to examples of the disclosure.
Figure 6B:
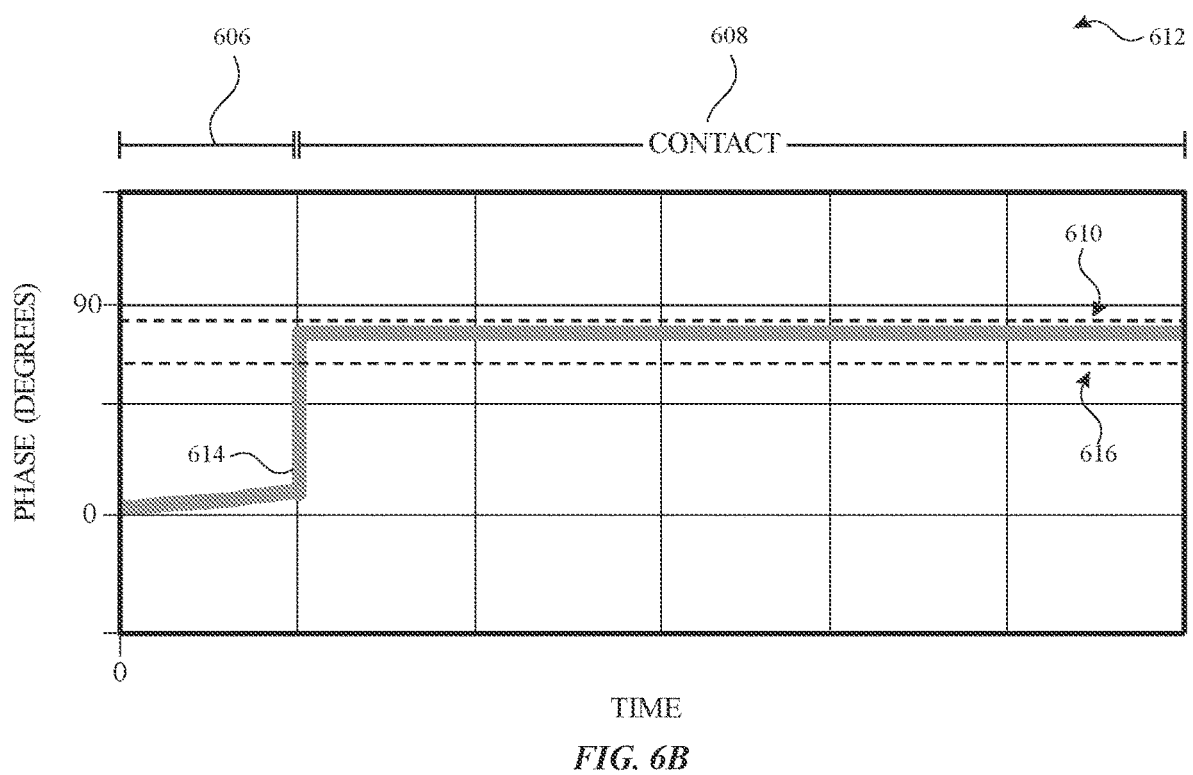

The above description of contact detection relies on amplitude. However, in some examples, the system is configured to use phase differences and/or amplitude to determine whether the wearable device is in contact with the user's skin, submerged in water, or none of the above. In some examples, the amount of phase change due to water or due to contact can be different, and the difference in phase can be used to differentiate between the contact and submerged conditions. For example, FIGS. 6A-6B illustrate example plots of the phase characteristic of the output measured in response to the stimulation signals according to examples of the disclosure. Plot 602 illustrates a phase signal measurement during two periods, including a baseline period 606 (e.g., before submersion) and a submerge period 618. Plot 612 also illustrates a phase signal measurement during two periods, including a baseline period 606 (e.g., before contact) and a contact period 608. Plots 602 and 612 also include two threshold phase characteristics, including first threshold 616 and second threshold 610. As illustrated in plots 602 and 612, the phase signal measurements 604/614 change from approximate 0 degree to approximately 90 degrees (e.g., approximately 90 degree shift) as a result of contact or submersion. However, the difference in phase change can be used to differentiate between the contact and submerged conditions. For example, when the phase is determined to be greater than a first threshold phase (e.g., first threshold 616) and less than a second threshold (e.g., second threshold 610), the system (e.g., DSP 206, host processor 208) can determine that the measurement electrode is in contact with the user. When the amplitude is greater than the first threshold phase (e.g., first threshold 616) and greater than the second threshold phase (e.g., second threshold 610), the system can determine that the measurement electrode is submerged. When the phase is less than the first and second threshold phases, the system can determine that the measurement electrode is not contacted nor submerged. The first threshold amplitude and the second threshold amplitude can be determined, for example, based on empirical study of expected range of load impedance from skin-to-electrode coupling and under water submersion conditions.

In some examples, phase difference can be utilized because the phase difference can provide a more accurate measurement than the amplitude (e.g., the separation in phase between contact and submerged conditions is greater than the separation in amplitude between the contact and submerged conditions). On the other hand, the amplitude of the output voltage can be a robust measurement and may degrades less quickly in the presence of interference. Thus, the system can consider both phase and amplitude differences to robustly differentiate between contact and submerge conditions.

Figure 7:
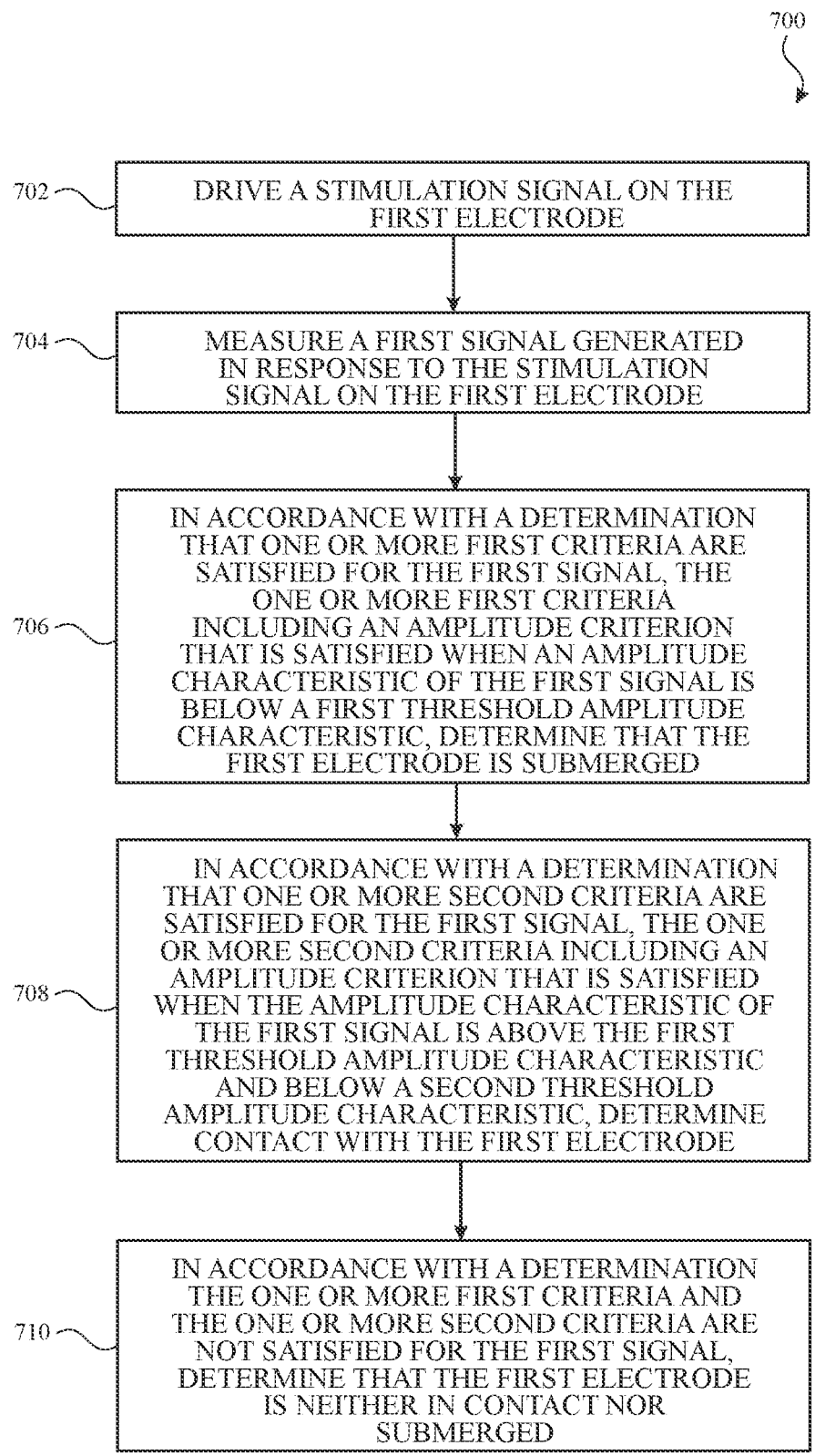
FIG. 7 illustrates an example process of classifying signals according to examples of the disclosure.

FIG. 7 illustrates an example process 700 of detecting contact or submerge according to examples of the disclosure. At 702, the system can drive a stimulation signal on a first electrode. In some examples, the stimulation signal (e.g., test signal 431) can be driven by a stimulation circuit (e.g., test signal circuit 430) that is coupled to the measurement electrode 402 (e.g., similar to the test signal circuitry described with respect to FIGS. 4A-4B).

At 704, the system is configured to measure a first signal generated in response to the stimulation signal on the first electrode. In some examples, the first signal can be a resulting test signal (e.g., resulting stimulation signal) that can be measured by sense circuitry. In some examples, the sense circuitry can be a buffer coupled to a stimulation circuit and the measurement electrode (e.g., buffer 424). In some examples, the resulting test signal can be measured from the output of a differential amplifier (e.g., differential amplifier 422).

In accordance with a determination that one or more first criteria are satisfied for the first signal, the one or more first criteria including an amplitude criterion that is satisfied when an amplitude characteristic of the first signal is below a first threshold amplitude characteristic, such as threshold 510, the system is configured, at 706, to determine that the first electrode is submerged. For example, plot 502 in FIG. 5A shows amplitude signal measurement 504 at baseline 506 (e.g., before submergence), and then a drop in the amplitude signal measurement 504 indicating submergence 508. In some examples, amplitude criterion is satisfied when the amplitude characteristic of the first signal is below both the first threshold amplitude characteristic and a second threshold amplitude characteristic, such as threshold 512.

In accordance with a determination that the one or more second criteria are satisfied for the first signal, the one or more second criteria including an amplitude criterion that is satisfied when the amplitude characteristic of the first signal is above the first threshold amplitude characteristic, such as threshold 510, and below a second threshold amplitude characteristic, such as threshold 512, the system is configured, at 708, to determine contact with the first electrode. For example, plot 514 in FIG. 5B shows amplitude signal measurement 516 at baseline 506 (e.g., before contact), and then a drop in the amplitude signal measurement 516 indicating contact 518.

In accordance with a determination the one or more first criteria and the one or more second criteria are not satisfied for the first signal, the system is configured, at 710, to determine that the first electrode is neither in contact nor submerged. For example, plots 502 and 514 in FIGS. 5A-5B show amplitude signal measurement 504/516 at baseline 506 above threshold 512 and above threshold 510 indicative of the first electrode is neither in contact nor submerged.

In some examples, the system is configured to drive the stimulation signal on a second electrode, different from the first electrode, such as reference electrode 404/448 in FIGS. 4A-4C (e.g., in addition to the first electrode, such as measurement electrode 402/446). In some examples, the first electrode is implemented in the crown 162 of the wearable device 150 as shown in FIGS. 1A and 1B. In some examples, the second electrode is implemented on a backside of the wearable device, such as the wearable device 150 in FIG. 1B. In some examples, the stimulation signal(s) can be driven by one or more stimulation circuit(s) coupled to the measurement electrode 402/446 or reference electrode 404/448 (e.g., test signal 431, complementary stimulation signals, S1 and S2).

In some examples, the system is configured to measure a second signal generated in response to the stimulation signal on the second electrode. In some examples, the second signal can be a resulting test signal (e.g., resulting stimulation signal) that can be measured by sense circuitry. In some examples, the sense circuitry can be a buffer coupled to a stimulation circuit and the measurement electrode (e.g., buffer 426/460). In some examples, the resulting test signal can be measured from the output of a differential amplifier (e.g., differential amplifier 422, 462).

In accordance with a determination that the one or more first criteria are satisfied for the second signal, the system is configured to determine that the second electrode is submerged. In accordance with a determination that one or more second criteria are satisfied for the second signal, the system is configured to determine contact with the second electrode. In accordance with a determination the one or more first criteria and the one or more second criteria are not satisfied for the second signal, the system is configured to determine that the second electrode is neither in contact nor submerged. In some examples, the first and second electrodes must be determined to be submerged in order to trigger a submerge or water mode. In some examples, a submerge or water mode can be triggered when either the first or second electrodes are determined to be submerged.

In some examples, the one or more second criteria include a phase criterion that is satisfied when a phase characteristic of the first signal is above a first threshold phase characteristic and below a second threshold phase characteristic. For example, plot 612 in FIG. 6B shows phase signal measurement below a first threshold (e.g., threshold 610) and above a second threshold (e.g., threshold 616), when in the contact period 608. In some examples, the one or more first criteria include a phase criterion that is satisfied when the phase characteristic of the first signal is above the second threshold phase characteristic and above the first threshold phase characteristic. For example, plot 602 in FIG. 6A shows phase signal measurement 604 above a first threshold and a second threshold (e.g., thresholds 610, 616) when in the submerge period 618. When neither submerged or in contact, the phase can be below the first and the second threshold phase characteristic.

It is understood from the description and illustrations of FIGS. 5A-5B and 6A-6B, that amplitude and/or phase criteria can be used. Thus, although FIG. 7 illustrates the use of amplitude criteria, that phase criteria can additionally or alternatively be used.

Figure 8:
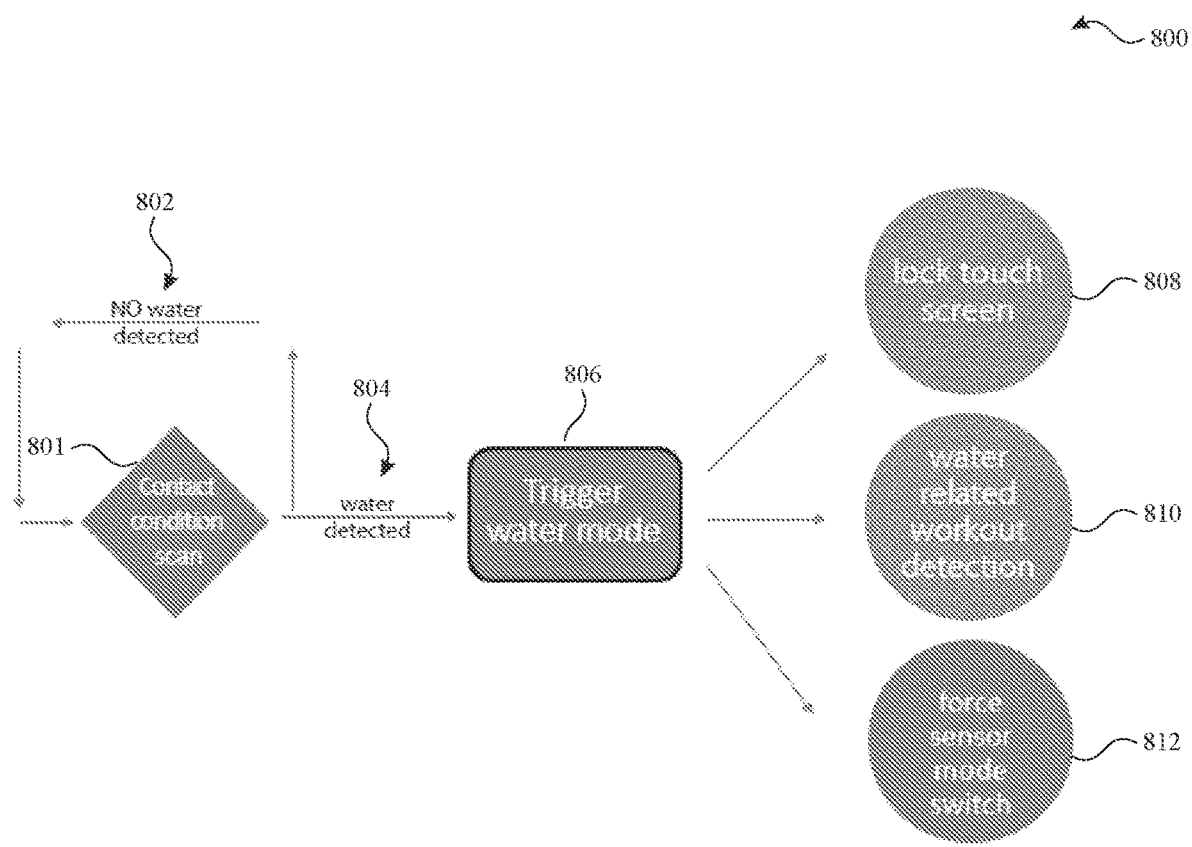
FIG. 8 is a flow diagram of a process for performing one or more device modes according to examples of the disclosure.

FIG. 8 illustrates an example flow diagram 800 for water detection and changing device operation in response to detecting water according to examples of the disclosure. At 801, the system performs a contact condition scan (e.g., driving a stimulation and detecting response) to determine whether the device is submerged. In some examples, the scan includes driving the stimulation signal on the first electrode and/or the second electrode, such as one or more of measurement or reference electrodes. In some examples, the scan 801 is performed continuously on a periodic basis (e.g., once per 1, 3, 5, 7, 10, 15, 20, 30, 50, or 60 seconds). In accordance with a determination that no water is detected (802), the system remains in the initial state (e.g., no-water state). In accordance with a determination that water is detected (804), the system is configured to trigger a water mode 806. In some examples, in response to determining that the first electrode is submerged (or that multiple electrodes are submerged, the system is configured to change a rate of driving the stimulation signal on the first electrode and/or the second electrode. For example, the scan 801 is optionally performed less often (e.g., once per 20 seconds, 30 seconds, 50 seconds, 60 seconds, 2 minutes, or 5 minutes). In accordance with a determination that the first electrode is submerged, the system is configured to initiate a process to disable capacitance sensing of the device (e.g. lock touch screen 152 at 808), initiate a process to detect water related activity (e.g. water related workout detection 810), and/or initiate a process to transition the touch screen (e.g., touch screen 152) to a force sensing mode (e.g., force sensor mode switch 812).

As discussed above, aspects in of the present technology include the gathering and use of signal information. The technology may be implemented along with technologies that involve gathering personal data that relates to the user's health and/or uniquely identifies or can be used to contact or locate a specific person. Such personal data can include demographic data, date of birth, location-based data, telephone numbers, email addresses, home addresses, and data or records relating to a user's health or level of fitness (e.g., vital signs measurements, medication information, exercise information, etc.).

The present disclosure recognizes that a user's personal data, including physiological information, such as data generated and used by the present technology, can be used to the benefit of users. For example, a user's heart rate may allow a user to track or otherwise gain insights about their health or fitness levels.

The present disclosure contemplates that the entities responsible for the collection, analysis, disclosure, transfer, storage, or other use of such personal data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should require receipt of the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. The policies and practices may be adapted depending on the geographic region and/or the particular type and nature of personal data being collected and used.

Despite the foregoing, the present disclosure also contemplates examples in which users selectively block the collection of, use of, or access to, personal data, including physiological information. For example, a user may be able to disable hardware and/or software elements that collect physiological information. Further, the present disclosure contemplates that hardware and/or software elements can be provided to prevent or block access to personal data that has already been collected. Specifically, users can select to remove, disable, or restrict access to certain health-related applications collecting users' personal health or fitness data.

Therefore, according to the above, some examples of the disclosure are directed a device. The device can comprise sensing circuitry configured to sense a first electrode; a stimulation circuit configured to drive a stimulation signal on the first electrode; and processing circuitry coupled to the sensing circuitry, the processing circuitry configured to: measure a first signal generated in response to the stimulation signal on the first electrode. In accordance with a determination that one or more first criteria are satisfied including an amplitude criterion that is satisfied when an amplitude characteristic of the first signal is below a first threshold amplitude characteristic, the processing circuitry is configured to determine that the first electrode is submerged. In accordance with a determination that one or more second criteria are satisfied including the amplitude criterion that is satisfied when the amplitude characteristic of the first signal is above the first threshold amplitude characteristic and below a second threshold amplitude characteristic, the processing circuitry is configured to determine contact with the first electrode and in accordance with a determination the one or more first criteria and the one or more second criteria are not satisfied, the processing circuitry is configured to determine that the first electrode is neither in contact nor submerged.

Additionally or alternatively, in some examples, the sensing circuitry includes a second sensing circuit configured to sense a second electrode. Additionally or alternatively, in some examples, the stimulation circuit is configured to drive the stimulation signal on the second electrode and the processing circuitry is further configured to: measure a second signal generated in response to the stimulation signal on the second electrode. In some examples, in accordance with a determination that the one or more first criteria are satisfied for the second signal, the processing circuitry is configured to determine that the second electrode is submerged. In accordance with a determination that the one or more second criteria are satisfied for the second signal, the processing circuitry is configured to determine contact with the second electrode and in accordance with a determination the one or more first criteria and the one or more second criteria are not satisfied for the second signal, the processing circuitry is configured to determine that the second electrode is neither in contact nor submerged.

Additionally or alternatively, in some examples, the one or more first criteria include a phase criterion that is satisfied when a phase characteristic of the first signal is above a first threshold phase characteristic and above a second threshold phase characteristic. Additionally or alternatively, in some examples, the one or more second criteria include a phase criterion that is satisfied when the phase characteristic of the first signal is above the second threshold phase characteristic and below the first threshold phase characteristic.

Additionally or alternatively, in some examples, the processing circuitry can be further configured to in accordance with a determination that the first electrode is submerged, initiate a process to disable a capacitive sensing of a touch screen of the device. In some embodiments, the processing circuitry can be further configured to in accordance with a determination that the first electrode is submerged, initiate a process to transition the touch screen to a force sensing mode. In some embodiments, the processing circuitry can be further configured to in accordance with a determination that the first electrode is submerged, initiate a process to detect water related activity. In some examples, the first electrode is implemented in a crown of a wearable device or on a backside of the wearable device. Additionally or alternatively, in some examples, the processing circuitry can be further configured to in response to determining that the first electrode is submerged, change a rate of driving the stimulation signal on the first electrode.

In some embodiments, the device can comprise sensing circuitry configured to sense a first electrode; a stimulation circuit configured to drive a stimulation signal on the first electrode; and processing circuitry coupled to the sensing circuitry, the processing circuitry configured to: measure a first signal generated in response to the stimulation signal on the first electrode. In accordance with a determination that one or more criteria are satisfied, the one or more criteria including an amplitude criterion that is satisfied when an amplitude characteristic of the first signal is below a first threshold amplitude characteristic and a phase criterion that is satisfied when a phase characteristic of the first signal is above a first threshold phase characteristic, the processing circuitry is configured to determine that the first electrode is submerged.

In some embodiments, the device can comprise sensing circuitry configured to sense a first electrode; a stimulation circuit configured to drive a stimulation signal on the first electrode; and processing circuitry coupled to the sensing circuitry, the processing circuitry configured to: measure a first signal generated in response to the stimulation signal on the first electrode. In accordance with a determination that one or more first criteria are satisfied for the first signal, the one or more first criteria including a phase criterion that is satisfied when a phase characteristic of the first signal is above a first threshold phase characteristic and above a second threshold phase characteristic, the processing circuitry is configured to determine that the first electrode is submerged. In accordance with a determination that one or more second criteria are satisfied for the first signal including a phase criterion that is satisfied when the phase characteristic of the first signal is below the first threshold phase characteristic and above the second threshold phase characteristic, the processing circuitry is configured to determine contact with the first electrode and in accordance with a determination the one or more first criteria and the one or more second criteria are not satisfied for the first signal, the processing circuitry is configured to determine that the first electrode is neither in contact nor submerged.

Some examples of the disclosure are directed to a method. The method can comprise measuring a first signal generated in response to the stimulation signal on the first electrode, in accordance with a determination that one or more first criteria are satisfied including an amplitude criterion that is satisfied when an amplitude characteristic of the first signal is below a first threshold amplitude characteristic, determining that the first electrode is submerged, in accordance with a determination that one or more second criteria are satisfied including the amplitude criterion that is satisfied when the amplitude characteristic of the first signal is above the first threshold amplitude characteristic and below a second threshold amplitude characteristic, determining contact with the first electrode and in accordance with a determination the one or more first criteria and the one or more second criteria are not satisfied, determining that the first electrode is neither in contact nor submerged.

Additionally or alternatively, the method further comprises measuring a second signal generated in response to the stimulation signal on the second electrode, in accordance with a determination that the one or more first criteria are satisfied for the second signal, determining that the second electrode is submerged and in accordance with a determination that the one or more second criteria are satisfied for the second signal, determining contact with the second electrode and in accordance with a determination the one or more first criteria and the one or more second criteria are not satisfied for the second signal, determining that the second electrode is neither in contact nor submerged.

Additionally or alternatively, in some examples, a method is provided, the method comprising measuring a first signal generated in response to the stimulation signal on the first electrode. In accordance with a determination that one or more criteria are satisfied, the one or more criteria including an amplitude criterion that is satisfied when an amplitude characteristic of the first signal is below a first threshold amplitude characteristic and a phase criterion that is satisfied when a phase characteristic of the first signal is above a first threshold phase characteristic, the method includes determining that the first electrode is submerged.

In some embodiments, a method is provided, the method comprising measuring a first signal generated in response to the stimulation signal on the first electrode. In accordance with a determination that one or more first criteria are satisfied for the first signal, the one or more first criteria including a phase criterion that is satisfied when a phase characteristic of the first signal is above a first threshold phase characteristic and above a second threshold phase characteristic, the method includes determining that the first electrode is submerged. In accordance with a determination that one or more second criteria are satisfied for the first signal including a phase criterion that is satisfied when the phase characteristic of the first signal is below the first threshold phase characteristic and above the second threshold phase characteristic, the method includes determining contact with first electrode and in accordance with a determination the one or more first criteria and the one or more second criteria are not satisfied for the first signal, the method includes determining that the first electrode is neither in contact nor submerged.

Some examples of the disclosure are directed to non-transitory computer readable storage medium. The non-transitory computer readable storage medium can store instructions, which when executed by a device comprising a first measurement electrode and one or more processing circuits, cause the one or more processing circuits to perform any of the methods disclosed above.

Some embodiments of the disclosure are directed to an electronic device, comprising one or more processors, memory, and means for performing any of the methods disclosed above.

Some embodiments of the disclosure are directed to an information processing apparatus for use in an electronic device, the information processing apparatus comprising means for performing any of the methods disclosed above.

Although examples of this disclosure have been fully described with reference to the accompanying drawings, it is to be noted that various changes and modifications will become apparent to those skilled in the art. Such changes and modifications are to be understood as being included within the scope of examples of this disclosure as defined by the appended claims.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the invention and its practical applications, to thereby enable others skilled in the art to best use the invention and various described embodiments with various modifications as are suited to the particular use contemplated.

The invention claimed is:

1. A device comprising:
sensing circuitry including a first sensing circuit configured to sense a first electrode;
a stimulation circuit configured to drive a stimulation signal on the first electrode; and
processing circuitry coupled to the sensing circuitry, the processing circuitry configured to:
measure a first signal generated in response to the stimulation signal on the first electrode;
in accordance with a determination that one or more first criteria are satisfied for the first signal, the one or more first criteria including a phase criterion that is satisfied when a phase characteristic of the first signal is above a first threshold phase characteristic and above a second threshold phase characteristic, determine that the first electrode is submerged;
in accordance with a determination that one or more second criteria are satisfied for the first signal including a phase criterion that is satisfied when the phase characteristic of the first signal is below the first threshold phase characteristic and above the second threshold phase characteristic, determine contact with the first electrode; and
in accordance with a determination the one or more first criteria and the one or more second criteria are not satisfied for the first signal, determine that the first electrode is neither in contact nor submerged.

2. The device of claim 1, the processing circuitry further configured to:
in accordance with a determination that the first electrode is submerged, initiate a process to disable capacitance sensing of a touch screen of the device.

3. The device of claim 1, the processing circuitry further configured to:
in accordance with a determination that the first electrode is submerged, initiate a process to transition a touch screen of the device to a force sensing mode.

4. The device of claim 1, the processing circuitry further configured to:
in accordance with a determination that the first electrode is submerged, initiate a process to detect water related activity.

5. The device of claim 1, wherein the first electrode is implemented in a crown of a wearable device.

6. The device of claim 1, wherein the first electrode is implemented on a backside of a wearable device.

7. The device of claim 1, the processing circuitry further configured to:
in accordance with a determination that the first electrode is submerged, change a rate of driving the stimulation signal on the first electrode.

8. The device of claim 1, the one or more first criteria further including:
an amplitude criterion that is satisfied when an amplitude characteristic of the first signal is below a first threshold amplitude characteristic.

9. The device of claim 8, the one or more second criteria further including:
an amplitude criterion that is satisfied when the amplitude characteristic of the first signal is above the first threshold amplitude characteristic and below a second threshold amplitude characteristic.

10. The device of claim 1, wherein:
the sensing circuitry including a second sensing circuit configured to sense a second electrode;
the stimulation circuit configured to drive the stimulation signal on the second electrode; and
the processing circuitry further configured to:
measure a second signal generated in response to the stimulation signal on the second electrode;
in accordance with a determination that the one or more first criteria are satisfied for the second signal, determine that the second electrode is submerged;
in accordance with a determination that the one or more second criteria are satisfied for the second signal, determine contact with the second electrode; and
in accordance with a determination the one or more first criteria and the one or more second criteria are not satisfied for the second signal, determine that the second electrode is neither in contact nor submerged.

11. A method comprising:
measuring a first signal generated in response to a stimulation signal on a first electrode;
in accordance with a determination that one or more first criteria are satisfied for the first signal, the one or more first criteria including a phase criterion that is satisfied when a phase characteristic of the first signal is above a first threshold phase characteristic and above a second threshold phase characteristic, determining that the first electrode is submerged;
in accordance with a determination that one or more second criteria are satisfied for the first signal including a phase criterion that is satisfied when the phase characteristic of the first signal is below the first threshold phase characteristic and above the second threshold phase characteristic, determining contact with the first electrode; and
in accordance with a determination the one or more first criteria and the one or more second criteria are not satisfied for the first signal, determining that the first electrode is neither in contact nor submerged.

12. The method of claim 11, further comprising:
in accordance with a determination that the first electrode is submerged, initiating a process to disable capacitance sensing of a touch screen of a device.

13. The method of claim 11, further comprising:
in accordance with a determination that the first electrode is submerged, initiating a process to transition a touch screen of a device to a force sensing mode.

14. The method of claim 11, further comprising:
in accordance with a determination that the first electrode is submerged, initiating a process to detect water related activity.

15. The method of claim 11, further comprising:
in accordance with a determination that the first electrode is submerged, changing a rate of driving the stimulation signal on the first electrode.

16. A non-transitory computer readable storage medium storing one or more programs, the one or more programs comprising instructions, which when executed by one or more processors of an electronic device, cause the electronic device to:
measure a first signal generated in response to a stimulation signal on a first electrode;
in accordance with a determination that one or more first criteria are satisfied for the first signal, the one or more first criteria including a phase criterion that is satisfied when a phase characteristic of the first signal is above a first threshold phase characteristic and above a second threshold phase characteristic, determine that the first electrode is submerged;

in accordance with a determination that one or more second criteria are satisfied for the first signal including a phase criterion that is satisfied when the phase characteristic of the first signal is below the first threshold phase characteristic and above the second threshold phase characteristic, determine contact with the first electrode; and in accordance with a determination the one or more first criteria and the one or more second criteria are not satisfied for the first signal, determine that the first electrode is neither in contact nor submerged.

17. The non-transitory computer readable storage medium of claim 16, the one or more programs comprising instructions further cause the electronic device to:

in accordance with a determination that the first electrode is submerged, initiate a process to disable capacitance sensing of a touch screen of the device.

18. The non-transitory computer readable storage medium of claim 16, the one or more programs comprising instructions further cause the electronic device to:

in accordance with a determination that the first electrode is submerged, initiate a process to transition a touch screen of the device to a force sensing mode.

19. The non-transitory computer readable storage medium of claim 16, the one or more programs comprising instructions further cause the electronic device to:

in accordance with a determination that the first electrode is submerged, initiate a process to detect water related activity.

20. The non-transitory computer readable storage medium of claim 16, the one or more programs comprising instructions further cause the electronic device to:

in accordance with a determination that the first electrode is submerged, change a rate of driving the stimulation signal on the first electrode.

* * * * *